US009040559B2

(12) United States Patent
Cuenoud et al.

(10) Patent No.: US 9,040,559 B2
(45) Date of Patent: *May 26, 2015

(54) BETA2-ADRENOCEPTOR AGONISTS

(71) Applicant: Novartis AG, Basel (CH)

(72) Inventors: Bernard Cuenoud, Horsham (GB); Ian Bruce, Horsham (GB); Robin Alec Fairhurst, Horsham (GB); David Beattie, Horsham (GB)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/450,692

(22) Filed: Aug. 4, 2014

(65) Prior Publication Data

US 2014/0343091 A1    Nov. 20, 2014

Related U.S. Application Data

(60) Continuation of application No. 14/076,478, filed on Nov. 11, 2013, now Pat. No. 8,796,307, which is a continuation of application No. 13/858,308, filed on Apr. 8, 2013, now Pat. No. 8,658,673, which is a continuation of application No. 13/555,536, filed on Jul. 23, 2012, now Pat. No. 8,436,017, which is a continuation of application No. 13/295,426, filed on Nov. 14, 2011, now Pat. No. 8,283,362, which is a continuation of application No. 12/885,922, filed on Sep. 20, 2010, now Pat. No. 8,067,437, which is a continuation of application No. 12/577,855, filed on Oct. 13, 2009, now Pat. No. 7,820,694, which is a division of application No. 11/074,400, filed on Mar. 7, 2005, now Pat. No. 7,622,483, which is a division of application No. 10/009,008, filed as application No. PCT/EP00/05058 on Jun. 2, 2000, now Pat. No. 6,878,721.

(30) Foreign Application Priority Data

Apr. 6, 1999    (GB) .................................. 9913083.3

(51) Int. Cl.
A61K 31/395    (2006.01)
A61K 31/4709    (2006.01)
C07C 215/80    (2006.01)
C07C 233/43    (2006.01)
C07C 311/08    (2006.01)
C07D 215/227    (2006.01)
C07D 215/26    (2006.01)
C07D 405/12    (2006.01)
A61K 45/06    (2006.01)

(52) U.S. Cl.
CPC ........... *A61K 31/4709* (2013.01); *C07C 215/80* (2013.01); *C07C 233/43* (2013.01); *C07C 311/08* (2013.01); *C07C 2102/08* (2013.01); *C07D 215/227* (2013.01); *C07D 215/26* (2013.01); *C07D 405/12* (2013.01); *A61K 45/06* (2013.01)

(58) Field of Classification Search
USPC ......................................... 514/312
See application file for complete search history.

(56) References Cited

U.S. PATENT DOCUMENTS 5,510,376 A    4/1996    Epstein et al.
5,578,638 A    11/1996    Brazzell et al.
(Continued)

FOREIGN PATENT DOCUMENTS

EP    0286278    10/1988
EP    0399422    11/1990
EP    0608568    8/1994
(Continued)

OTHER PUBLICATIONS

Eidebenz et al., Ber, vol. 74B, pp. 1798-1801, 1941.
Mitrochkine Anton A et al., "Enantioselective Synthesis of cis- and trans-2(S)-Amino-1-d-indane: Debrominative [1,2]-Hydride Shift Rearrangement by Reduction of cis-2-Azido-1-bromoindane with LiAID4", J. Org. Chem, vol. 62, pp. 6204-6209, 1997.
(Continued)

*Primary Examiner* — Bruck Kifle
(74) *Attorney, Agent, or Firm* — Daniel Woods

(57) ABSTRACT

Compounds of formula

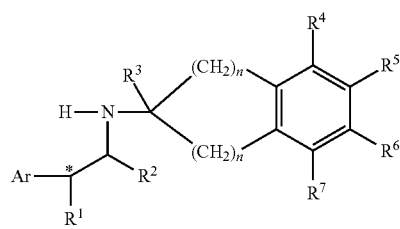

I in free or salt or solvate form, where
Ar is a group of formula

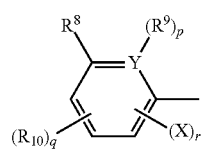

II

Y is carbon or nitrogen and $R^1$, $R^2$, $R^3$, $R^4$, $R^5$, $R^6$, $R^7$, $R^8$, $R^9$, $R^{10}$, X, n, p, q and r are as defined in the specification, their preparation and their use as pharmaceuticals, particularly for the treatment of obstructive or inflammatory airways diseases.

13 Claims, No Drawings

(56) References Cited

U.S. PATENT DOCUMENTS 5,594,027 A  1/1997  Epstein et al.
5,977,154 A  11/1999  Bell et al.

FOREIGN PATENT DOCUMENTS

| EP | 0882704 | 8/1997 |
| EP | 0894787 | 10/1997 |
| EP | 1300407 | 4/2003 |
| JP | 03 261755 | 11/1991 |
| JP | 93/18007 | 9/1993 |
| JP | 07002831 | 1/1995 |
| JP | 09501429 | 2/1997 |
| JP | 99/09001 | 2/1999 |
| JP | 2002512639 | 4/2002 |
| WO | WO 92/18461 | 10/1992 |
| WO | WO 93/15041 | 8/1993 |
| WO | WO 95/04713 | 2/1995 |
| WO | WO 99/51564 | 10/1999 |
| ZA | 987425 | 8/1998 |

OTHER PUBLICATIONS

Cannon, Joseph G., "Conformationally Restricted Congeners of Dopamine Derived from 2-Aminoindan", J. Med. Chem., vol. 25, pp. 1442-1446, 1982.

Sindelar et al., "2-Amino-4,7-dimethoxyindan Derivatives: Synthesis and Assessment of Dopaminergic and Cardiovascular Actions", J. Med. Chem., vol. 25, pp. 858-864, 1982.

Chemical Abstract AN 1994:217308, WO 93/18007, Tauchlya et al., 1993.

Banitt et al., Monofluoromethanesulfonalides, A new Series of Bronchodiators, Journal of Medicinal Chemistry, vol. 17, No. 1, 1974.

BETA2-ADRENOCEPTOR AGONISTS

This is a continuation of application Ser. No. 13/555,536 filed on Jul. 23, 2012, which is a continuation of application Ser. No. 13/295,426 filed on Nov. 14, 2011 which is a continuation of application Ser. No. 12/885,922 filed on Sep. 20, 2010, which is a continuation of application Ser. No. 12/577,855 filed on Oct. 13, 2009, which is a divisional of application Ser. No. 11/074,400 filed on Mar. 7, 2005, which is a divisional of application Ser. No. 10/009,008, which is a 371 of PCT/EP00/05058 filed on Jun. 2, 2000, the entire disclosures of which are hereby incorporated by reference.

This invention relates to organic compounds, their preparation and that use as pharmaceuticals.

The invention provides in one aspect a compound of formula

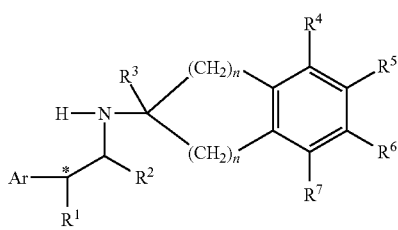

I in free or salt or solvate form, where
Ar is a group of formula

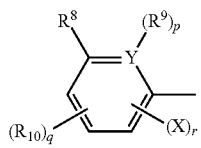

II $R^1$ is hydrogen, hydroxy, or alkoxy,
$R^2$ and $R^3$ are each independently hydrogen or alkyl,
$R^4$, $R^5$, $R^6$ and $R^7$ are each independently hydrogen, halogen, cyano, hydroxy, alkoxy, aryl, alkyl, alkyl substituted by one or more halogen atoms or one or more hydroxy or alkoxy groups, alkyl interrupted by one or more hetero atoms, alkenyl, trialkylsilyl, carboxy, alkoxycarbonyl, or —$CONR^{11}R^{12}$ where $R^{11}$ and $R^{12}$ are each independently hydrogen or alkyl, or $R^4$ and $R^5$, $R^5$ and $R^6$, or $R^6$ and $R^7$ together with the carbon, atoms to which they are attached denote a carbocyclic or heterocyclic ring,
$R^8$ is halogen, —$OR^{13}$, —$CH_2OR^{13}$ or —$NHR^{13}$ where $R^{13}$ is hydrogen, alkyl, alkyl interrupted by one or more hetero atoms, —$COR^{14}$, where $R^{14}$ is hydrogen, —$N(R^{15})R^{16}$, alkyl or alkyl interrupted by one or more hetero atoms, or aryl and $R^{15}$ and $R^{16}$ are each independently hydrogen, alkyl or alkyl interrupted by one or more hetero atoms, or $R^{13}$ is —$C(=NH)R^{17}$, —$SOR^{17}$ or —$SO_2R^{17}$ where $R^{17}$ is alkyl or alkyl interrupted by one or more hetero atoms, and
$R^9$ is hydrogen, or $R^8$ is —$NHR^{18}$ where —$NHR^{18}$ and $R^9$, together with the carbon atoms to which they are attached, denote a 5- or 6-membered heterocycle,
$R^{10}$ is —$OR^{19}$ or —$NHR^{19}$ where $R^{19}$ is hydrogen, alkyl, alkyl interrupted by one or more hetero atoms, or —$COR^{20}$, where $R^{20}$ is —$N(R^{21})R^{22}$, alkyl or alkyl interrupted by one or more hereto atoms, or aryl, and $R^{21}$ and $R^{22}$ are each independently hydrogen, alkyl or alkyl interrupted by one or more hetero atoms,
X is halogen, or halomethyl or alkyl,
Y is carbon or nitrogen,
n is 1 or 2,
p is zero when Y is nitrogen or 1 when Y is carbon,
q and r are each zero or 1, the sum of q+r or 2; and
the carbon atom marked with an asterisk * has the R or S configuration, or a mixture thereof, when $R^1$ is hydroxy or alkoxy.

Terms used in this specification have the following meanings:

"Alkyl" denotes straight chain or branched alkyl, which may be, for example, $C_1$ to $C_{10}$ alkyl such as methyl, ethyl, n-propyl, isopropyl, n-butyl, isobutyl, sec-butyl, tert-butyl, straight or branched pentyl, straight or branched hexyl, straight or branched heptyl, straight or branched nonyl or straight or branched decyl. Preferably alkyl is $C_1$ to $C_4$ alkyl. Alkyl substituted by one or more halogen atoms or one or more hydroxy or alkoxy groups may be any of the above $C_1$ to $C_{10}$ alkyl groups substituted by one or more halogen, preferably fluorine or chlorine, atoms, by one or more hydroxy groups or by one or more $C_1$ to $C_{10}$, preferably $C_1$ to $C_4$, alkoxy groups.

"Alkyl interrupted by one or more hetero atoms" denotes straight chain or branched alkyl e.g. $C_2$ to $C_{10}$ alkyl, in which one or more pairs of carbon atoms are linked by —O—, —NR—, —S—, —S(=O)— or —$SO_2$—, where R is hydrogen or $C_1$ to $C_{10}$ (preferably $C_1$ to $C_4$) alkyl. Preferred such groups are alkoxyalkyl groups, preferably $C_1$-$C_4$-alkoxy-$C_1$-$C_4$-alkyl groups.

"Alkoxy" denotes straight chain or branched alkoxy and may be, for example, $C_1$ to $C_{10}$ alkoxy such as methoxy, ethoxy, n-propoxy, isopropoxy, n-butoxy, isobutoxy, sec-butoxy, tert-butoxy, or straight or branched, pentoxy, hexyloxy, heptyloxy, octyloxy, nonyloxy or decyloxy. Preferably alkoxy is $C_1$ to $C_4$ alkoxy.

"Alkenyl" means straight chain or branched alkenyl, which may be unsubstituted or substituted, for example by one or more halogen atoms or one or more alkoxy groups, and which may be, for example, $C_2$ to $C_{10}$ alkenyl such as vinyl, 1-propenyl, 2-propenyl, 1-butenyl, isobutenyl, or straight or branched pentenyl, hexenyl, heptenyl, octenyl, nonenyl or decenyl. Preferred alkenyl is $C_2$ to $C_4$ alkenyl.

"Aryl" denotes unsubstituted or substituted aryl, e.g. unsubstituted phenyl or naphthyl, or phenyl or naphthyl substituted by one or more, e.g. 1 to 4, substituents selected from $C_1$-$C_4$-alkyl, hydroxy, $C_1$-$C_4$-alkoxy, halogen, or halo-$C_1$-$C_4$-alkyl. Preferably, aryl is unsubstituted phenyl or phenyl substituted by 1 or 2 substituents selected from $C_1$-$C_4$-alkyl or halogen.

"Alkylene" denotes straight chain or branched, alkylene which may be, for example, $C_1$-$C_{10}$-alkylene such as methylene, ethylene, 1,2-propylene, 1,3-propylene, butylene, pentylene, hexylene, heptylene, octylene, nonylene or decylene. Preferably alkylene is $C_1$-$C_4$-alkylene.

"Alkenylene" denotes straight chain or branched alkenylene which, may be, for example, $C_2$-$C_{10}$-alkenylene such as vinylene, propenylene, butenylene, pentenylene, hexenylene, heptenylene, octenylene, nonenylene or decenylene. Preferably alkenylene is $C_2$-$C_4$-alkenylene.

In formula I, n is 1 or 2, i.e. there are 2 or 4 $CH_2$ groups in the ring fused to the indicated benzene ring, so that ring is either a 5-membered or 7-membered ring.

The group Ar in formula II in which $R^8$ is —$NHR^{18}$ and —$NHR^{18}$ and $R^9$ together denote a 5- or 6-membered heterocycle may be, for example, a group in which Y is carbon, $R^8$ is —$NHR^{18}$ and —$NHR^{18}$ and $R^9$ together denote
a group of formula —NH—CO—$R^{23}$— where $R^{23}$ is an alkylene or alkyleneoxy group,
a group of formula —NH—$SO_2$—$R^{24}$ where $R^{24}$ is an alkyleneoxy group,
a group of formula —NH—$R^{25}$($COOR^{26}$)— where $R^{25}$ is an alkylene or alkenylene group and $R^{26}$ is alkyl, or
a group of formula —NH—CO—NH— or —NH—CO—S—,
$R^{19}$ is —$OR^{19}$ where $R^{19}$ is as hereinbefore defined,
X is alkyl,
p is 1, 1 is 1 and r is zero or 1.

The alkylene, alkenylene and alkyleneoxy groups preferably have 1 to 4 carbon atoms.

Preferred groups Ar of formula II is which $R^8$ is —$NHR^{18}$, and —$NHR^{18}$ and $R^9$ together denote a 5- or 6-membered heterocycle, include groups in which
Y is carbon, $R^8$ is and —$NHR^{18}$ and $R^9$ together denote group of formula —NH—CO—C($R^{27}$)=C($R^{28}$)— or —NH—CO—$CH_2$—O— or —NH—CO—$CH_2$— or —NH—$SO_2$—$CH_2$—O— or —NH—C($COOR^{26}$)=CH— or —NH—CO—NH— or —NH—CO—S— where $R^{27}$ and $R^{28}$ are each independently hydrogen or $C_1$-$C_4$-alkyl and $R^{26}$ is $C_1$-$C_4$-alkyl, $R^{10}$ is —OH, X is $C_1$-$C_4$-alkyl, p is 1, q is 1 and r is zero or 1.

More preferred groups Ar of formula II where $R^8$ is —$NHR^{18}$, and —$NHR^{18}$ and $R^9$ together denote a 5- or 6-membered heterocycle include those of the formulae

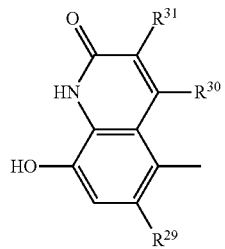

III

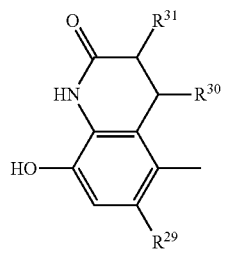

IIIa in which $R^{29}$, $R^{30}$ and $R^{31}$ are each independently hydrogen or $C_1$-$C_4$-alkyl,

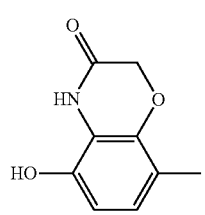

IV

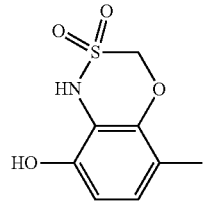

V

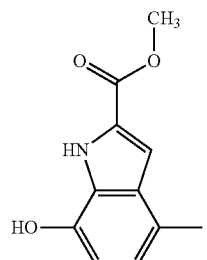

VI

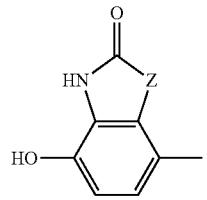

VII in which Z is —O—, —NH— or —S—.

The group Ar of formula II in which $R^8$ is halogen and $R^9$ is hydrogen may be, for example, a group of formula II in which Y is carbon, $R^8$ is halogen, preferably chlorine, $R^9$ is hydrogen, $R^{10}$ is —$NHR^{18}$ where $R^{18}$ is hydrogen or $C_1$-$C_4$-alkyl, preferably hydrogen or methyl, X is halogen or halomethyl, preferably chlorine or trifluoromethyl, and p, q and r are each 1. Preferred groups Ar among such groups include those of formulae

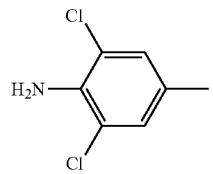

VIII

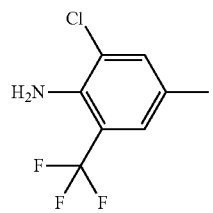

IX

The group Ar of formula II in which $R^8$ is —$OR^{13}$ and $R^9$ is hydrogen may be, for example, a group of formula II in which Y is carbon, $R^8$ is —$OR^{13}$ where $R^{13}$ is hydrogen, $C_1$-$C_4$-alkyl, $C_2$-$C_4$-alkoxy-$C_1$-$C_4$-alkyl, —$COR^{14}$ where $R^{14}$ is $C_1$-$C_4$-alkyl, $C_6$-$C_{10}$-aryl or —N($R^{15}$)$R^{16}$ where $R^{15}$ and $R^{16}$ are each independently hydrogen or $C_1$-$C_4$-alkyl, $R^{10}$ is —$OR^{19}$ or —$NHR^{19}$ where $R^{19}$ is hydrogen, $C_1$-$C_4$-alkyl, $C_1$-$C_4$-alkoxy-$C_1$-$C_4$-alkyl, or —$COR^{20}$ where $R^{20}$ is —N($R^{21}$)$R^{22}$, $C_1$-$C_4$-alkyl, $C_1$-$C_4$-alkoxy-$C_1$-$C_4$-alkyl or $C_6$-$C_{10}$-aryl and $R^{21}$ and $R^{22}$ are each independently hydrogen or $C_1$-$C_4$-alkyl, p and q are each 1 and r is zero. Preferred groups Ar among such groups include those of formulae

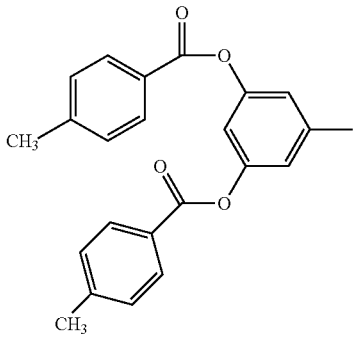

X

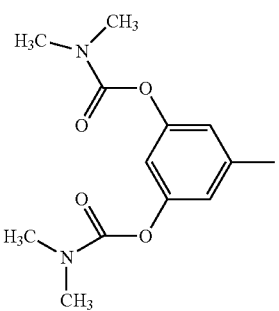

XI

The group Ar of formula II in which $R^8$ is —$CH_2OR^{13}$ may be, for example, a group of formula II in which Y is carbon, $R^8$ is —$CH_2OR^{13}$ where $R^{13}$ is hydrogen, $C_1$-$C_4$-alkyl, or $C_1$-$C_4$-alkoxy-$C_1$-$C_4$-alkyl, $R^9$ is hydrogen, $R^{10}$ is —$OR^{19}$ where $R^{19}$ is hydrogen, $C_1$-$C_4$-alkyl or $C_1$-$C_4$-alkoxy-$C_1$-$C_4$-alkyl or $R^{10}$ is —$NHR^{19}$ where $R^{19}$ is hydrogen, $C_1$-$C_4$-alkyl or —$COR^{20}$ where $R^{20}$ is $C_1$-$C_4$-alkyl, $C_6$-$C_{10}$-aryl or —$N(R^{21})R^{22}$ where $R^{21}$ and $R^{22}$ are each independently hydrogen or $C_1$-$C_4$-alkyl, p and q are each 1 and r is zero; or a group of formula in which Y is nitrogen, $R^8$ is —$CH_2OR^{13}$ where $R^{13}$ is hydrogen, $C_1$-$C_4$-alkyl or $C_1$-$C_4$-alkoxy-$C_1$-$C_4$-alkyl, $R^{10}$ is —$OR^{19}$ where $R^{19}$ is hydrogen, $C_1$-$C_4$-alkyl or $C_1$-$C_4$-alkoxy-$C_1$-$C_4$-alkyl, p and r are zero and q is 1. Preferred groups Ar among such groups include those of formulae

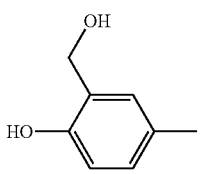

XII

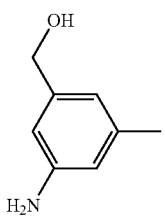

XIII

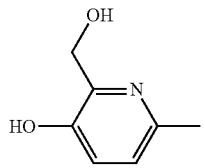

XIV

The group Ar of formula II in which $R^8$ is —$NHR^{13}$ may be, for example, a group of formula II in which Y is carbon, $R^8$ is —$NHR^{13}$ where $R^{13}$ is hydrogen, $C_1$-$C_{10}$ alkyl, $C_1$-$C_{10}$ alkyl interrupted by 1 to 3 hetero atoms, —$COR^{14}$ where $R^{14}$ is hydrogen, $C_1$-$C_{10}$-alkyl or $C_1$-$C_{10}$-alkyl interrupted by 1 to 3 hetero atoms, or $R^{13}$ is —$C(=NH)R^{17}$, —$SOR^{17}$ or —$SO_2R^{17}$ where $R^{17}$ is $C_1$-$C_{10}$-alkyl or $C_1$-$C_{10}$-alkyl interrupted by 1 to 3 hetero atoms, $R^9$ is hydrogen, $R^{10}$ is —$OR^{18}$ where $R^{18}$ is hydrogen, $C_1$-$C_4$-alkyl or $C_1$-$C_4$-alkoxy-$C_1$-$C_4$ alkyl, p and q are each 1 and r is zero. Preferred groups Ar among such groups include those of formula

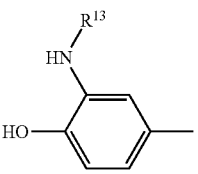

XV especially those where $R^{13}$ is hydrogen, $C_1$-$C_4$-alkyl, —$COR^{14}$ where $R^{14}$ is hydrogen or $C_1$-$C_4$-alkyl or $R^{13}$ is —$SO_2R^{17}$ where $R^{17}$ is $C_1$-$C_4$-alkyl.

Especially preferred groups Ar are those of formulae III, IV, V, XII and XV as hereinbefore defined.

The group $R^1$ is formula I may be, for example, hydrogen, hydroxy or $C_1$-$C_4$-alkoxy such as methoxy, ethoxy, isopropoxy, n-butoxy or tert-butoxy. Preferably, $R^1$ is hydroxy.

When $R^1$ is hydroxy or alkoxy, the carbon atom in formula I marked with an asterisk * preferably has the R configuration.

The groups $R^2$ and $R^3$ in formula I may be, for example, each independently hydrogen or $C_1$-$C_4$-alkyl, e.g. methyl or ethyl. In most of the preferred embodiments of the invention, $R^2$ is hydrogen and $R^3$ is hydrogen or methyl.

The groups $R^4$, $R^5$, $R^6$ and $R^7$ in formula I may be, for example, each independently hydrogen, chlorine, fluorine, chloromethyl, trifluoromethyl, hydroxy, $C_1$-$C_{10}$-alkoxy, $C_1$-$C_{10}$-alkyl, $C_1$-$C_{10}$-alkyl interrupted by one or more oxygen or sulfur atoms or one or more NH, SO or $SO_2$ groups, $C_2$-$C_4$-alkenyl, trimethylsilyl, triethylsilyl, phenyl, carboxy, $C_1$-$C_4$-alkoxycarbonyl, —$CONR^{11}R^{12}$ (where $R^{11}$ and $R^{12}$ are each independently hydrogen or $C_1$-$C_4$-alkyl), or $R^4$ and $R^5$ and $R^6$ or $R^6$ and $R^7$, together with the carbon atoms to which they are attached, may denote a 5- or 6-membered carbocyclic ring, which is preferably a cycloaliphatic ring which is preferably saturated, or a 5- or 6-membered O-heterocyclic ring containing one or two oxygen atoms. Preferably, $R^4$, $R^5$, $R^6$ and $R^7$ are each hydrogen or are such that the benzene ring to which they are attached is symmetrically substituted, i.e. either (a) $R^4$ and $R^7$ are identical and $R^5$ and $R^6$ are identical or together denote a symmetrical ring, or (b) $R^4$ and $R^5$ together and $R^6$ and $R^7$ together denote identical rings. More preferably, $R^4$ and $R^7$ are identical and are each hydrogen, $C_1$-$C_4$-alkyl or $C_1$-$C_4$-alkoxy, and either $R^5$ and $R^6$ are identical and are each hydrogen, $C_1$-$C_4$-alkyl, $C_1$-$C_4$- alkoxy or $C_1$-$C_4$-alkoxy-$C_1$-$C_4$-alkyl, or $R^5$ and $R^6$ together denote —$(CH_2)_s$— or —$O(CH_2)_tO$— where s is 3 or 4 and t is 1 or 2.

Especially preferred compounds of the invention include compounds of formula I in which Ar is a group of formula III, IV, V, XII or XV, $R^1$ is hydroxy, $R^2$ and $R^3$ are hydrogen, and $R^4$ and $R^7$ are identical and are each hydrogen, $C_1$-$C_4$-alkyl, $C_1$-$C_4$-alkoxy, and either $R^5$ and $R^6$ are identical and are each hydrogen, $C_1$-$C_4$-alkyl, $C_1$-$C_4$-alkoxy or $C_1$-$C_4$-alkoxy-$C_1$-$C_4$-alkyl, or $R^5$ and $R^6$ together denote —$(CH_2)_4$— or —$O(CH_2)_2O$—, in free or salt or solvate form. In such compounds, the carbon atom in formula I marked with an asterisk * preferably has the R configuration. Specific especially preferred compounds are those described in the Examples hereinafter.

The compounds of formula (I) are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid or hydroiodic acid, nitric acid, sulfuric acid, phosphoric acid; and organic acids such as formic acid, acetic acid, propionic acid, butyric acid, benzoic acid, o-hydroxybenzoic acid p-hydroxybenzoic acid, p-chlorobeozoic acid, diphenylacetic acid, triphenylacetic acid, 1-hydroxynaphthalene-2-carboxylic acid, 3-hydroxynaphthalene-2-carboxylic acid, aliphatic hydroxy acids such as lactic acid, citric acid, tartaric acid or malic acid, dicarboxylic acids such as fumaric acid, maleic acid or succinic acid, and sulfonic acids such as methanesulfonic acid or benzenesulfonic acid. These salts may be prepared from compounds of formula I by known salt-forming procedures.

Suitable solvates are pharmaceutically acceptable solvates, preferably hydrates.

The present invention also provides a process for the preparation of compounds of formula I in free or salt or solvate form. They can be prepared by a process comprising:

(a) for the preparation of a compound, where $R^1$ is hydroxy, either (i) reacting a compound of formula

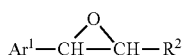

XVI with a compound of formula

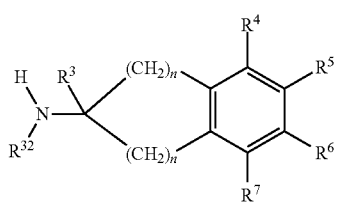

XVII where $Ar^1$ is Ar as hereinbefore defined or a protected form thereof, $R^2$, $R^3$, $R^4$, $R^5$, $R^6$, $R^7$ and n are as hereinbefore defined and $R^{32}$ is hydrogen, or an amine-protective group, or (ii) reducing a compound of formula

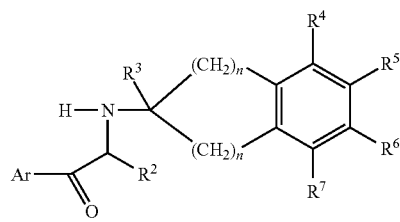

XVIII where $Ar^1$, $R^2$, $R^3$, $R^4$, $R^5$, $R^6$ and $R^7$ are as hereinbefore defined, so convert the indicated keto group into —CH(OH)—; or (b) for the preparation of a compound where $R^1$ is hydrogen, reducing a corresponding compound of formula I where $R^1$ is hydroxy; or (c) for the preparation of a compound of formula I where $R^1$ is alkoxy, either (i) O-alkylating a corresponding compound of formula I where $R^1$ is hydroxy or (ii) reacting a corresponding compound having a leaving moiety instead of $R^1$ with an alcohol of formula $R^1H$ where $R^1$ is alkoxy;

and, optionally, converting a resultant compound of formula I in protected form into a corresponding compound in unprotected form;

and recovering the resultant compound of formula I in free or salt or solvate form.

Process variant (a)(i) may be carried out using known procedures for epoxide-amine reactions. It is conveniently carried out without a solvent or in an inter solvent, for example a hydrocarbon such as toluene or an alcohol such as n-butanol. The reaction temperature is conveniently from 25° C. to 200° C., preferably from 80° C. to 150° C. The temperature may be achieved by conventional heating or by microwave irradiation.

Process variant (a)(ii) may be carried out using conventional methods, for example by reaction with sodium borohydride under conventional conditions.

Process variant (b) may be carried out using known procedures for reduction of secondary alcohols to hydrocarbons. Process variant (c)(i) may be carried out using known procedures for O-alkylation, for example by reaction with an alkylating agent such as an alkyl halide under known conditions. Process variant (c)(ii) may be effected using known procedures for benzylic displacement reactions, the leaving moiety being e.g. tosylate, mesylate, halogen or hydroxy.

Compounds of formula I in free form may be converted into salt or solvate forms, and vice versa, in a conventional manner.

Compounds of the invention can be recovered from the reaction mixture and purified in a conventional manner. Isomers, such as enantiomers, may be obtained in a conventional manner, e.g. by fractional crystallization or asymmetric synthesis from corresponding asymmetrically substituted, e.g. optically-active, starting materials.

Compounds of formula XVI are known compounds or can be prepared by processes analogous to those used for the preparation of the known compounds, for example the procedures described in Journal of Medicinal Chemistry 1987, 30, 1563-1566. Compounds of formula XVI in which the carbon atom indicated by the asterisk * is chiral may be prepared from a compound of formula

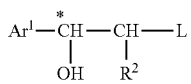   XIX where $Ar^1$ and $R^2$ are as hereinbefore defined and L is a leaving atom or group, as described in WO95/25104.

Compounds of formula XVI may alternatively be prepared by epoxidation of a compound of formula

   XX where $Ar^1$ and $R^2$ are as hereinbefore defined, using conventional procedures, such as those used in the Examples hereinafter.

Compounds of formula XX are known or may be prepared by methods analogous to those used for the preparation of known compounds, for example those used in the Examples hereinafter.

Compounds of formula XVII are known or may be prepared by methods analogous to those used for the preparation of the known compounds. $R^{32}$ as an amine-protective group in formula XVII may be a known such group, for example as described in Protective Groups in Organic Synthesis, T. W. Greene, P. G. M. Wuts, John Wiley & Sons Inc. Second Edition, 1991, preferably benzyl or trifluoroacetyl.

For example, compounds of formula XVII, where $R^5$ is hydrogen, may be prepared by reducing an oxime of formula

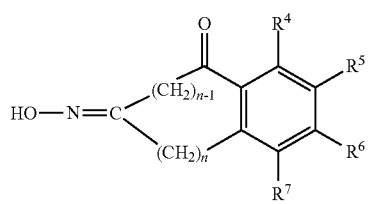   XXI where $R^4$, $R^5$, $R^6$, and $R^7$ and n are as hereinbefore defined. The reduction may be carried out by conventional methods for reducing oximes to amines. For example, the reduction may be carried out by catalytic hydrogenation, preferably using palladium on charcoal as the catalyst. The hydrogenation may be effected using known procedures, for example as described by R. D. Sindelar et al, J. Med. Chem. (1982), 25(7), 858-864. Oximes of formula XXI may be prepared as described by Sindelar et al, op. cit., or by analogous procedures.

Compounds of formula XVII where $R^4$ and $R^7$ are hydrogen can be prepared by reacting a compound of formula

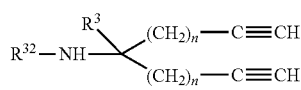   XXII with a compound of formula

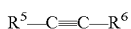   XXIII where $R^2$, $R^5$, $R^6$, $R^{32}$ and n are as hereinbefore defined. The reaction may be carried out in the presence of a catalyst such as tris(triphenylphosphine)rhodium chloride. The reaction temperature may be, for example, from 60 to 120° C. The reaction is conveniently carried out in an inert solvent, for example ethanol, when the reaction temperature is conveniently about the reflux temperature of the solvent. The reaction may be carried out using known procedures, for example as described in WO96/23760. Where $R^5$ and $R^6$ are trialkylsilyl, the reaction between the compounds of formulae XXII and XXIII may be carried out in the presence of a metal carbonyl complex catalyst, for example using the procedure described by K. P. C. Vollhardt and R. Hillard, J. Am. Chem. Soc. 1977, 99(12), 4058, or an analogous procedure. Compounds of formula XXII may be prepared as described in WO96/23760 or by analogous procedures. Compounds of formula XXIII are known or may be prepared by known procedures.

Compounds of formula XVII where $R^3$ is alkyl, particularly methyl, and n is 1 may be prepared by amination of the corresponding 2-alkyl-indan-1-one using ammonia and $K_3FeCN_6$, e.g. by the procedure of Fornum and Carlson, Synthesis 1972, 191.

Compounds of formula XVII as hereinbefore defined where $R^4$, $R^5$, $R^6$ and $R^7$ are such that the benzene ring to which they are attached is symmetrically substituted are novel, other than the compounds where $R^4$, $R^5$, $R^6$, and $R^7$ and $R^{30}$ are each hydrogen, where $R^4$ and $R^7$ are methyl or methoxy when $R^5$, $R^6$ and $R^{30}$ are each hydrogen, and where $R^4$, $R^7$ and $R^{30}$ are hydrogen when $R^5$ and $R^6$ are each hydroxy, fluorine or chlorine. In particular, preferred intermediates of formula XVII are novel where (i) $R^4$ and $R^7$ are each hydrogen and $R^5$ and $R^6$ are either each $C_2$-$C_4$-alkyl, $C_2$-$C_4$-alkoxy, $C_1$-$C_4$-alkoxy-$C_1$-$C_4$-alkyl or $R^5$ and $R^6$ together denote —$(CH_2)_s$— or —$((CH_2)_tO$— where s is 1 to 4 and t is 1 or 2; or (ii) $R^4$ and $R^7$ are each $C_2$-$C_4$-alkyl or $C_2$-$C_4$-alkoxy and $R^5$ and $R^6$ are either each hydrogen, $C_1$-$C_4$-alkyl, $C_1$-$C_4$-alkoxy and $R^5$ and $R^6$ are either each hydrogen, $C_1$-$C_4$-alkyl, $C_1$-$C_4$-alkoxy, or $C_1$-$C_4$-alkoxy-$C_1$-$C_4$-alkyl or $R^5$ and $R^6$ together denote —$(CH_2)_s$— or —$O(CH_2)_tO$— where s is 1 to 4 and t is 1 or 2.

Compounds of formula XVIII are novel compounds which may be prepared by reaction of a compound of formula

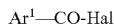   XXIV where $Ar^1$ is as hereinbefore defined and Hal is a halogen atom, preferably chlorine or bromide, with a compound of formula XVII as hereinbefore defined. The reaction may be carried out using conventional procedures, for example those described by Yoshizaki et al, J. Med. Chem (1976), 19(9), 1138-42.

Where desired, the protection of any reactive group may be carried out at any appropriate stage in the above processes. The protecting group is suitably one used conventionally in the art and may be introduced and removed using conventional procedure. For example, when a hydroxy group in $Ar^1$ is protected by a benzyl group, the latter may be removed by catalytic hydrogenation in the presence of palladium on charcoal using conventional procedures, such as those used hereinafter in the Examples.

Compounds of formula I in free, salt or solvate form are useful as pharmaceuticals. Accordingly the invention also provides a compound of formula I in free, salt or solvate form for use as a pharmaceutical. The compounds of formula I in free, salt or solvate form, hereinafter referred to alternatively as "agents of the invention", have good β2-adrenoceptor agonist activity. The β2 agonist activity, onset of action and duration of action of the agents of the invention may be tested using the guinea pig tracheal strip in vitro assay according to the procedure of R. A. Coleman and A. T. Nials, J. Pharmacol. Methods (1989), 21(1) 71-86. The binding potency and selectivity for the β2-adrenoreceptor relative to the β1-adrenoreceptor can be measured by a classical filtration binding assay according to the procedure of Current Protocols in Pharmacology (S. J. Enna (editor-in-chief) et al, John Wiley & Son, Inc, 1998), or by cAMP determination in cells expressing β2- or β1-adrenoreceptor, according to the procedure of B. January et al, British J. Pharmacol 123: 701-711 (1998).

The agents of the invention commonly have a rapid onset of action and have a prolonged stimulating action on the β2-adrenoreceptor, compounds of the Examples hereinbelow having Ki (β2) values of the order of 0.1 to 1000 nM, having durations of action of the order of 1 to greater than 12 hours, and having binding selectivities for the β2-adrenoreceptor relative to the β1-adrenoreceptor from 1.5 to 500. For example, the compounds of Examples 1, 2, 4, 5, 6, 8, and 27 have β2 and β1 binding potencies, measured by cAMP determination in cells expressing β2- and β1-adrenoreceptors, represented by $EC_{50}$ values (β2/β1) (in nM) of 0.92/9.52, 0.23/1.25, 6.07/14.5, 0.79/6.10, 0.3/3.60, 0.57/8.46 and 0.012/0.5 respectively. The compounds of Examples 2, 4, 5, 27 and 29 have T(50%) times (in minutes) of >400 at 71 nM concentration, 82 at 100 nM, 444 at 100 nM, 222 at 1.0 nM and 279 at 10 nM respectively in the guinea pig tracheal strip assay, where T(50%) is the time for inhibition of contraction to decay to 50% of its maximum value.

Having regard to their β2 agonist activity, the agents of the invention are suitable for use to the treatment of any condition which is prevented or alleviated by activation of the β2-adrenoreceptor. In view of their long acting selective β2 agonist activity, the agents of the invention are useful in the relaxation of bronchial smooth muscle and the relief of bronchoconstriction. Relief of bronchoconstriction can be measured in models such as the in vivo plethysmography models of Chong et al, J. Pharmacol. Toxicol. Methods 1998, 39, 163-168, Hammelmann et al, Am. J. Respir. Crit. Care Med., 1997, 156, 766-775 and analogous models. The agents of the invention are therefore useful is the treatment of obstructive or inflammatory airways diseases. In view of their long duration of action, it is possible to administer the agents of the invention once-a-day in the treatment of such diseases. In another aspect, agents of the invention commonly exhibit characteristics indicating a low incidence of side effects commonly encountered with β2 agonists such as tachycardia, tremor and restlessness, such agents accordingly being suitable for use in on demand (rescue) treatment as well as prophylactic treatment of obstructive or inflammatory airways diseases.

Treatment of a disease in accordance with the invention may be symptomatic or prophylactic treatment. Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now offers identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid), or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant form any previously administered symptomatic asthma therapy.

Other inflammatory or obstructive airways diseases and conditions to which the present invention is applicable include adult respiratory distress syndrome (ARDS), chronic obstructive pulmonary or airways-disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Having regard to their β2 agonist activity the agents of the invention, are also useful in the treatment of a condition requiring relaxation of smooth muscle of the uterus or vascular system. They are thus useful for the prevention or alleviation of premature labour pains in pregnancy. They are also useful in the treatment of chronic and acute urticaria, psoriasis, allergic conjunctivitis, actinitis, hay fever, and mastocytosis.

The agents of the invention are also useful as co-therapeutic agents for use in conjunction with anti-inflammatory or bronchodilatory drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with the anti-inflammatory or bronchodilatory drug in a fixed pharmaceutical composition or it may be administered separately, before, simultaneously with or after the anti-inflammatory or bronchodilatory drug. Such anti-inflammatory drugs include steroids, in particular glucocorticosteroids such, as budesonide, beclamethasone, fluticasone or mometasone, and dopamine receptor agonists such as cabergoline, bromocriptine or ropinirole. Such bronchodilatory drugs include anticholinergic or antimuscarinic agents, in particular ipratropium bromide, oxitropium bromide and triotropium bromide. Combinations of agents of the invention and steroids may be used, for example, in the treatment of COPD or, particularly, asthma. Combinations of agents of the invention and anticholinergic or antimascarinic agents or dopamine receptor agonists may be used, for example, in the treatment of asthma or, particularly, COPD.

In accordance with the foregoing, the present invention also provides a method for the treatment of an obstructive or inflammatory airways disease which comprises administering to a subject, particularly a human subject, in need thereof a compound of formula I, or a pharmaceutically acceptable salt or solvate thereof, as hereinbefore described. In another aspect, the invention provides a compound of formula I, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases.

In a further aspect, the invention also provides a pharmaceutical composition comprising a compound of formula I in free form, or in the form of a pharmaceutically acceptable salt or solvate thereof, optionally together with a pharmaceutically acceptable diluent or carrier therefor. Such compositions may be prepared using conventional diluents or excipients and techniques known is the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations.

The invention also includes (A) a compound of formula I as hereinbefore described in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound is inhalable form.

Dosages employed in practising the invention will of course vary depending, for example, on the particular condition to be treated, the effect desired and the mode of administration. In general, suitable daily dosages for administration by inhalation are of the order of from 1 to 5000 µg.

The invention illustrated by the following Examples. Compounds used in the Examples are prepared as follows:

Intermediate 1

5,6-Diethyl-indan-2-ylamine hydrochloride

Preparation 1

3-chloro-1-(3,4-diethylphenyl)-1-propanone 1,2-Diethylbenzene (10.9 g, 74.6 mmol) and propionyl chloride (9.7 g, 74.6 mmol) are added dropwise to AlCl$_3$ (22.3 g, 167.8 mmol) in nitromethane (75 mL) over 30 min. The reaction mixture is stirred at room temperature for 2 hours, after which 70 g of ice and 14 mL concentrated sulphuric acid are added. The aqueous phase is extracted with ether, and the combined organic phases extracted with 2N HCl and saturated aqueous NaCl. The organic phase is further treated with activated charcoal, magnesium sulphate, and filtered, and the solvent removed in vacuo.

1H-NMR (CDCl$_3$) ppm: 7.8 (1H, s, Ar); 7.7 (1H, d, Ar); 7.2 (1H, d, Ar); 3.9 (2H, t, CH$_2$); 3.4 (2H, t, CH$_2$); 2.8 (4H, q, CH$_2$CH$_3$); 1.2 (6H, m, CH$_3$).

Preparation 2

2,3-dihydro-5,6-diethyl-1H-inden-1-one 3-chloro-1-(3,4-diethylphenyl)-1-propanone (15.5 g) is dissolved in 66 mL concentrated sulphuric acid and heated to 90° C. for 4 hours. The reaction mixture is cooled, ice (70 g) is added, and the aqueous solution extracted twice with toluene. The organic layer is washed with sodium bicarbonate, saturated aqueous NaCl, and treated with activated charcoal and magnesium sulphate. After filtration, the solvent is removed in vacuo. The product is purified by flash column chromatography (silica, hexane/ethylacetate 10:1), and further crystallised in hexane.

1H-NMR (CDCl3) ppm: 7.6 (1H, s, Ar); 7.3 (1H, d, Ar); 3.1 (2H, m, CH$_2$); 2.7 (6H, m, CH$_2$+CH$_2$CH$_3$); 1.2 (6H, m, CH$_3$).

Preparation 3

5,6-Diethyl-3-oxime-1H-indene-1,2(3H)-dione 2,3-Dihydro-5,6-diethyl-1H-inden-1-one (5 g, 26 mmol) in methanol (75 mL) is brought to 40° C., n-butyl nitrite (3.0 g, 28.6 mmol) is added dropwise, followed by the addition of concentrated HCl (1.25 mL). After 1 hour, the reaction is brought to room temperature and the precipitated product filtered off, washed with ice-cold methanol and dried.

1H-NMR (d6-DMSO) ppm: 12.6 (1H, s, OH); 7.4 (1H, s, Ar); 7.3 (1H, d, Ar); 3.6 (2H, s, CH$_2$); 2.6 (4H, m, CH$_2$CH$_3$); 1.1 (6H, m, CH$_3$).

Preparation 4

5,6-Diethyl-indan-2-ylamine hydrochloride 5,6-Diethyl-3-oxime-1H-inden-1,2(3H) (4.5 g) is added to a mixture of acetic acid (150 ml), and concentrated sulphuric acid (4.5 mL). Pd/C 5% (1.5 g) is added, the reaction mixture degassed with nitrogen, and hydrogenated for 5 hours. The catalyst is then removed by filtration, the pH brought to pH 10 with 4M NaOH, and the solution extracted with chloroform. The organic phase is dried with magnesium sulphate, and the solvent removed in vacuo. The residue is redissolved in a minimum amount of ether, and HCl saturated ether added. The white precipitate is filtered and dried to yield the HCl salt of 5,6-diethyl-indan-2-ylamine, a compound of formula XVII where $R^3$, $R^4$ and $R^7$ are H, $R^5$ and $R^6$ are each CH$_3$CH$_2$—, $R^{30}$ hydrogen and n is 1.

1H-NMR (d6-DMSO) ppm: 8.7 (3H, bd s, NH$_3$); 7.3 (2H, s, Ar); 4.2 (1H, bd s, CH); 3.5 (2H, dd, CH$_2$); 3.3 (2H, dd, CH$_2$) 2.8 (4H, q, CH$_2$CH$_3$); 1.4 (6H, t, CH$_3$).

Other compounds of formula XVII are prepared by procedures analogous to those used for Intermediate 1 or starting from available compounds and using procedures analogous to Preparations 3 and 4. These compounds of formula XVII are shown in the following table, $R^3$ being hydrogen and n being 1 for all compounds.

| Intermediate | $R^4$ | $R^5$ | $R^6$ | $R^7$ |
|---|---|---|---|---|
| 2 | CH$_3$CH$_2$ | H | H | CH$_3$CH$_2$ |
| 3 | H | —(CH$_2$)$_4$— | | H |
| 4 | H | —O(CH$_2$)$_2$O— | | H |
| 5 | H | CH$_3$(CH$_2$)$_3$ | CH$_3$(CH$_2$)$_3$ | H |
| 6 | H | CH$_3$(CH$_2$)$_2$ | CH$_3$(CH$_2$)$_2$ | H |
| 7 | H | CH$_3$O | CH$_3$O | H |

Intermediate 2: ES + MS m/e (MH+): 204
Intermediate 3: 1H-NMR (d6-DMSO) ppm: 8.1 (3H, bd s, NH$_3$); 6.9 (2H, s, Ar); 3.9 (1H, bd s, CH); 3.2 (2H, dd, CH$_2$); 2.8 (2H, dd, CH$_2$); 2.7 (4H, m, CH$_2$Ar); 1.7 (6H, t, CH$_2$).
Intermediate 4: 1H-NMR (d6-DMSO) ppm: 8.3 (3H, bds, NH$_3$); 6.85 (2H, s, Ar); 4.2 (4H, s, 2CH$_2$); 3.1 (2H, dd, CH$_2$); 2.85 (2H, dd, CH$_2$).
Intermediate 5: 1H-NMR (d6-DMSO) ppm: 6.9 (2H, s, Ar); 3.8 (1H, m, CH); 3.1 (2H, dd, CH$_2$); 2.6 (2H, dd, CH$_2$); 2.5 (4H, t, 2CH$_2$); 1.65 (2H, bds, NH$_2$); 1.55 (4H, m, 2CH$_2$); 1.4 (4H, m, 2CH$_2$); 0.95 (6H, t, CH$_3$).
Intermediate 6: 1H-NMR (d6-DMSO) ppm: 8.1 (3H, bd s, NH$_3$); 7.0 (2H, s, Ar); 3.9 (1H, bd s, CH); 3.2 (2H, dd, CH$_2$); 2.8 (2H, dd, CH$_2$); 2.5 (4H, q, EtCH$_2$Ar); 1.6 (4H, q, CH$_2$), 0.9 (6H, t, CH$_3$).
Intermediate 7: 1H-NMR (d6-DMSO) ppm: 8.3 (3H, bd s, NH$_3$); 6.9 (2H, s, H-Ar); 3.9 (1H, bd, m, CHN); 3.7 (6H, s, CH$_3$O), 3.2 (2H, dd, CH$_2$), 2.9 (2H, dd, CH$_2$).

Intermediate 8

2-(Trifluoroacetylamino)-5,6-bis(methoxymethyl) indane

According to the procedure of Magnus et. al (*Tetrahed. Lett.*, 34, 23-26 (1993)) a solution of commercially available 1,4-dimethoxy-2-butyne (1.32 g, 11.5 mmol) in nitrogen-degassed ethanol is heated to 80° C. with stirring under a nitrogen atmosphere. Tris(triphenylphosphine)rhodium chloride (64 mg, 0.07 mmol) and a solution of 2,2,2-trifluoro-N-[1-(2-propynyl)-3-butynyl]-acetamide (470 mg, 2.32 mmol; prepared from literature procedure; Romero, Arthur G.; Leiby, Jeffrey A PCT Int. Appl. WO 9623760) in nitrogen-degassed ethanol (2 ml) are added in portions over 2 hours. The mixture is stirred under nitrogen at 80° C. for a further 3 hours. The solvent is removed under vacuo and the residue is purified by flash chromatography on silica gel, elating with hexane/ethyl acetate (2:1)

$^1$H-NMR (CDCl$_3$) ppm: 2.9 (2H, dd), 3.35 (2H, dd), 3.45 (6H, s), 4.57 (4H, s), 4.85 (1H, m), 6.4 (1H, br s), 7.30 (2H, s).

Intermediate 9

2-Amino-5,6-bis(methoxymethyl)indane

A solution of potassium hydroxide (150 mg, 2.60 mmol) in water (0.5 ml) is added to a solution of 2-(trifluoroacety-lamino)-5,6-bis(methyoxymethyl)indane (240 mg, 0.75 mmol) in methanol (3 mL) and the mixture is heated at reflux for 2.5 hours. The solvent was removed in vacuo and the residue is partitioned between aqueous sodium hydroxide (10 mL) and ethyl acetate (20 mL). The organic extract is dried (MgSO$_4$) and the solvent is removed in vacuo to leave the product as a dark oil.

$^1$H-NMR (CDCl$_3$) ppm: 2.60 (2H, dd), 3.10 (2H, dd), 3.33 (6H, s), 3.75 (1H, m), 4.42 (4H, s), 7.17 (2H, s).

Intermediate 10

8-Hydroxy-5-[(indan-2-ylamino)-acetyl]-1H-quinolin-2-one 5-(Chloroacetyl)-8-hydroxy-2(1H)-quinolinone (25 mg, 0.105 mmol) prepared from literature procedure (Yoshizaki, Shiro; Tanimura, Kaoru; Tamada, Shigeharu; Yabuuchi, Youichi; Nakagawa, Kazuyuki, *J. Med. Chem.* (1976), 19(9), 1138-42) is reacted neat with indan-2-ylamine (205 mg, 1.21 mmol) at 2.5° C. for 2 hours. The reaction mixture is purified by flash chromatography (silica, CH$_2$Cl$_2$/methanol 9:1). ES+ MS m/e 335 (MH+).

Intermediate 11

This compound of formula XVIII where Ar is a group of formula III, R$^{27}$, R$^{28}$ and R$^{29}$ are hydrogen, R$^2$, R$^3$, R$^4$ and R$^7$ are hydrogen, and R$^5$ and R$^6$ are each methoxy, is prepared by a procedure analogous to that used for preparation of Intermediate 10. ES+MS m/e (MH$^+$): 395.

Intermediate 12

8-Benzyloxy-3-methyl-5-oxiranyl-1H-quinolin-2-one

8-Hydroxy-3-methyl-1H-quinolin-2-one is prepared according to the procedure of Wang et al (T.-C. Wang, Y.-L. Chen, K.-H. Lee, C.-C. Izeng *Synthesis* 1997, 87-90).

$^1$H-NMR (d4-CH$_3$OH) ppm: 2.14 (s, 3H), 6.84-6.89 (m, 1H), 6.95-7.03 (m, 2H), 6.90 (s, 1H), 7.71 (s, 1H).

8-Benzyloxy-3-methyl-1H-quinolin-2-one

Benzyl bromide (1.28 mL) is added to a suspension of potassium carbonate (2.98 g) in a solution of 8-hydroxy-3-methyl-1H-quinolin-2-one (1.26 g) in acetone (36 mL) at room temperature. The reaction mixture is refluxed for 18 hours, filtered, evaporated and purified by flash column chromatography on silica gel, during with 2% methanol in dichloromethane.

$^1$H-NMR (CDCl$_3$) ppm: 2.11 (s, 3H), 5.13 (s, 2H), 6.92-6.98 (m, 1H), 7.02-7.08 (m, 2H), 7.29-7.40 (m, 5H), 7.57 (s, 1H), 9.23 (s, 1H).

8-Benzyloxy-3-methyl-1H-quinolin-2-one

A solution of bromine (0.57 g) in acetic acid (2 mL) is added dropwise to a solution of 8-benzyloxy-3-methyl-1H-quinolin-2-one (0.94 g) and sodium acetate (0.96 g) in acetic acid (12 ml) at room temperature. The reaction mixture is stirred at room temperature for 3 hours, evaporated, the residue partitioned between water (5 mL) and ethyl acetate (5 mL), extracting a further 2× with ethyl acetate (5 mL). Combined organic extracts are dried over magnesium sulphate and purified by flash column chromatography on silica gel, eluting with 2% methanol in dichloromethane.

$^1$H-NMR (CDCl$_3$) ppm: 2.27 (s, 3H), 5.18 (s, 2H), 6.83 (d, 1H), 7.39 (d, 1H), 7.37-7.41 (m, 5H), 7.91 (s, 1H), 9.08 (s, 1H).

8-Benzyloxy-3-methyl-5-vinyl-1H-quinolin-2-one

Palladium tetrakis(triphenylphosphine) (30 mg) is added to a solution of 8-benzyloxy-5-bromo-3-methyl-1H-quinolin-2-one (239 mg) and tributylvinyltin (203 µL) in toluene (7 mL) at room temperature. Use reaction mixture is heated for 2 hours at 100° C., cooled to room temperature, evaporated and the product purified by flash column chromatography on silica gel, eluting with 2% ethyl acetate in dichloromethane.

$^1$H-NMR (CDCl$_3$) ppm: 2.24 (s, 3H), 5.18 (s, 2H), 5.32-5.39 (m, 1H), 5.61-5.68 (m, 1H), 6.95 (d, 1H), 7.09-7.20 (m, 1H), 7.21-7.26 (m, 2H), 7.31-7.43 (m, 4H), 7.89 (s, 1H), 9.20 (s, 1H).

8-Benzyloxy-3-methyl-5-oxiranyl-1H-quinolin-2-one

To 8-benzyloxy-3-methyl-5-vinyl-1H-quinolin-2-one (300 mg) is added to a 0.1M solution of dimethyldioxirane in acetone (12.4 mL). After stirring at room temperature for 2 hours, the solvent is removed in vacuo to yield the product.

$^1$H-NMR (CDCl$_3$) ppm: 2.23 (s, 3H), 2.77-2.81 (m, 1H), 3.18-3.23 (m, 1H), 4.17-4.21 (m, 1H), 5.18 (s, 2H), 6.91 (d, 1H), 7.01 (d, 1H), 7.93 (s, 1H), 9.10 (s, 1H).

Intermediate 13

8-Benzyloxy-5-[2(5,6-diethyl-indan-2-ylamino)-1-hydroxy-ethyl]-3-methyl-1H-quinolin-2-one A solution of Intermediate 12 (65 mg) and 5,6-diethyl-indan-2-ylamine (120 mg) in DMSO (1.5 mL) is heated for 18 hours at 90° C. The solvent is removed in vacuo, and the product purified by flash chromatography on silica gel, dating with 10% methanol in dichloromethane.

$^{13}$C-NMR (d4-CH$_3$OH) ppm: 15.96, 17.14, 26.33, 36.77, 53.34, 59.82, 67.33, 71.73, 112.09, 118.98, 121.73, 125.42, 128.74, 129.24, 129.47, 129.61, 131.84, 134.56, 137.52, 137.64, 142.29, 145.94, 164.02.

Intermediate 14

8-Methoxymethoxy-6-methyl-5-oxiranyl-1H-quinolin-2-one

8-Hydroxy-6-methyl-1H-quinolin-2-one is prepared according to the procedure of Wang et al (T.-C. Wang, Y.-L. Chen, K.-H. Lee, C.-C. Izeng *Synthesis* 1997, 87-90).

$^1$H-NMR (d6-DMSO) ppm: 2.26 (s, 3H), 6.45 (d, 1H), 6.79 (s, 1H), 6.90 (s, 1H), 7.78 (d, 1H).

5-Bromo-8-hydroxy-6-methyl-1H-quinolin-2-one

A 45% solution of hydrobromic acid in acetic acid (324 μL) is added dropwise to a solution of 8-hydroxy-6-methyl-1H-quinolin-2-one (316 mg) in dimethylsulphoxide (9 mL) at room temperature. The reaction mixture is allowed to stand for 18 hours at room temperature and the solvent removed in vacuo.

$^1$H-NMR (d6-DMSO) ppm: 2.33 (s, 3H), 6.58 (d, 1H), 6.92 (s, 1H), 8.03 (d, 1H), 10.44 (s, 1H), 10.67 (s, br, 1H).

5-Bromo-8-methoxymethoxy-6-methyl-1H-quinolin-2-one

Methoxymethyl chloride (410 μL) was added to a suspension of potassium carbonate (1.24 g) in a solution of 5-bromo-8-hydroxy-6-methyl-1H-quinolin-2-one (480 mg) in dimethylformamide (9 mL) at 0° C. The reaction mixture is stirred, for 18 hours at room temperature, filtered, the solvent removed in vacuo, and the product purified by flash column chromatography on silica gel, eluting with 2% methanol in dichloromethane.

$^{13}$C-NMR (CDCl$_3$) ppm: 23.42, 56.52, 95.07, 115.78, 116.19, 119.32, 123.30, 128.13, 132.14, 139.78, 141.78, 161.32.

8-Methoxymethoxy-6-methyl-5-vinyl-1H-quinolin-2-one

Bis-(triphenylphosphine)palladium (II) chloride (98 mg) is added to a solution of 5-bromo-8-methoxymethoxy-6-methyl-1H-quinolin-2-one (410 mg) and tributylvinyltin (603 μL) in dimethylformamide (14 mL) at room temperature. The reaction mixture is heated for 24 hours at 90° C., evaporated and purified by flash column chromatography on silica gel, eluting with 2% methanol in dichloromethane.

$^1$H-NMR (CDCl$_3$) ppm: 2.19 (s, 3H), 3.41 (s, 3H), 5.18 (d, 1H), 5.20 (s, 2H), 5.60 (d, 1H), 6.52 (d, 1H), 6.63-6.69 (m, 1H), 6.96 (s, 1H), 7.95 (d, 1H), 9.78 (s, 1H).

8-Methoxymethoxy-6-methyl-5-oxiranyl-1H-quinolin-2-one is obtained from 8-methoxymethoxy-6-methyl-5-vinyl-1H-quinolin-2-one (186 mg) according to the last step of the procedure for Intermediate 12.

$^1$H-NMR (CDCl$_3$) ppm: 2.38 (s, 3H), 2.68-2.72 (m, 1H), 3.19-3.23 (m, 1H), 3.43 (s, 3H), 3.97-4.01 (m, 1H), 5.21 (s, 2H), 6.60 (d, 1H), 6.98 (s, 1H), 8.22 (d, 1H), 9.09 (s, 1H).

Intermediate 15

(R)-2-(4-benzyloxy-3-nitrophenyl)-oxirane, is prepared according to the procedure of R. Hett et al, Tetrahedron Lett. (1997), 38(7), 1125-1128.

Intermediate 16

(S)-8-Benzyloxy-5-oxiranyl-1H-quinolin-2-one

8-Benzyloxy-5-((S)-2-chloro-1-hydroxy-ethyl)-1H-quinolin-2-one (S)-2-methyl-CBS-oxazaborolidine, 1M in toluene (0.30 mL, 0.30 mmol) is added to dry THF (tetrahydrofuran) (10 mL) in an oven dried flask. Borane-THF complex, 1M in THF (3.05 mL) is then added dropwise and the solution is stirred at room temperature for 15 minutes and then cooled to 0° C. 8-Benzyloxy-5-chloroacetyl-1H-quinolin-2-one (1.00 g), prepared as described in WO95/25104, is then added in small portions over a period of 30 minutes. The reaction mixture is stirred at 0° C. The reaction is shown to be complete by TLC (thin layer chromatography) after 15 minutes. The reaction mixture is quenched with methanol (1 mL), the solvent is removed in vacuo and the residue is partitioned between 0.2 M H$_2$SO$_4$ (100 mL) and CHCl$_3$ (100 mL). The organic layer is dried over MgSO$_4$, filtered and the solvent is removed in vacuo. Crystallized from ethyl acetate. TLC (silica, dichlormethane/methanol 25:1 R$_f$=0.30).

(S)-8-Benzyloxy-5-oxiranyl-1H-quinolin-2-one

8-Benzyloxy-5-((S)-2-chloro-1-hydroxy-ethyl)-1H-quinolin-2-one (0.55 g) is dissolved in acetone (20 mL). K$_2$CO$_3$ (0.58 g) is added and the reaction mixture is refluxed. The reaction is shown to be complete by TLC after 18 hours. The solvent is removed in vacuo and the residue is partitioned between ethyl acetate (100 mL) and water (100 mL). The organic layer is dried over MgSO$_4$, filtered and the solvent is removed in vacuo. The product is triturated with diethyl ether, filtered and dried. TLC (silica, dichloromethane/methanol 25.1 R$_f$=0.45).

Intermediate 17

6,7,8,9-Tetrahydro-5H-benzocyclohepten-7-ylamine

Benzyl-(6,7,8,9-tetrahydro-5H-benzocyclohepten-7-yl-amine 5,6,8,9-Tetrahydro-benzocyclohepten-7-one (3.00 g) and benzylamine (2.00 g) are dissolved in ethanol (50 mL). A catalytic amount of 10% palladium on charcoal is added and the reaction mixture is placed under an atmosphere of hydrogen. The reaction mixture is stirred at r.t. The reaction is shown to be complete by TLC after 24 hours. The catalyst is filtered off and the solvent is removed in vacuo. The product is not purified further. TLC (silica, n-hexane/ethyl acetate 1:2 R$_f$=0.50).

6,7,8,9-Tetrahydro-5H-benzocyclohepten-7-ylamine

Benzyl-(6,7,8,9-tetrahydro-5H-benzocyclohepten-7-yl)-amine (2.80 g) is dissolved in methanol (100 mL) and the composed is deprotected by adding a catalytic amount of 10% palladium on charcoal and placing the solution under an atmosphere of hydrogen. The reaction is shown to be complete by TLC after 24 hours. The catalyst is filtered off and the solvent is removed in vacuo. The product is not purified further. TLC (silica, dichloromethane/methanol 25:1 $R_f$=0.15).

Intermediate 18

Benzyl-(5,6-diethyl-indan-2-yl)-amine

N-(5,6-Diethyl-indan-2-yl)-benzamide 5,6-Diethyl-indan-2-ylamine (4.10 g) is dissolved in dichloromethane (DCM) (150 mL) and triethylamine (2.41 g) is added. Benzoyl, chloride (3.20 g) is then added dropwise and the reaction mixture is stirred at room temperature. The reaction is shown to be complete by TLC after 1 hour. The solution is washed with 0.2M HCl (100 mL), water (100 mL) and brine (100 mL). The organic layer is dried over MgSO$_4$, filtered and the solvent is removed in vacuo. Crystallised from ethyl acetate. TLC (silica, dichloromethane/methanol 10:1 $R_f$=0.85).

Benzyl-(5,6-diethyl-indan-2-yl)-amine

N-(5,6-Diethyl-indan-2-yl)-benzamide (3.30 g) is dissolved in dry THF (100 mL). Lithium aluminium hydride, 1M in THF (22.52 ml) is then added dropwise. Use reaction mixture is stirred at 50° C. The reaction is shown to be complete by TLC after 6 hours. The reaction mixture is allowed to cool, poured slowly into ice-water (200 mL) and extracted with diethyl ether (2×150 mL). The organic layer is dried over MgSO$_4$, filtered and the solvent is removed in vacuo. The product is not purified further. TLC (silica, n-hexane/ethyl acetate 2:1 $R_f$=0.20).

Intermediate 19

(R)-1-(3-Amino-4-benzyloxy-phenyl)-2-[benzyl-(5,6-diethyl-indan-2-yl)-amino]ethanol (R)-2-[Benzyl-(5,6-diethyl-indan-2-yl)-amino]-1-(4-benzyloxy-3-nitro-phenyl)-ethanol The title compound is prepared from Intermediate 15 (3.01 g) and Intermediate 18 (3.10 g) by an analogous procedure to that used to prepare (S)-8-Benzyloxy-5-[2-(5,6-diethyl-indan-2-ylamino)-1-hydroxy-ethyl]-1H-quinolin-2-one in Example 19. The reaction is shown to be complete by TLC after 24 hours. The product is purified by flash column chromatography (silica, n-hexane/ethyl acetate 4:1). TLC (silica, n-hexane/ethyl acetate 4:1 $R_f$=0.25).

(R)-1-(3-Amino-4-benzyloxy-phenyl)-2-[benzyl-(5,6-diethyl-indan-2-yl)-amino]ethanol (R)-2-[Benzyl-(5,6-diethyl-indan-2-yl)amino]-1-(4-benzyloxy-3-nitro-phenyl)-ethanol (3.00 g) is dissolved in THF (50 mL) and toluene (50 mL). A catalytic amount of PtO$_2$ is added and the solution is stirred under an atmosphere of H$_2$. The reaction is shown to be complete by TLC after 6 hours. The catalyst is filtered off and the solvent is removed in vacuo. The product is not purified further. TLC (silica, n-hexane/ ethyl acetate 1:1 $R_f$=0.75).

Intermediate 20

1-(3-Amino-4-benzyloxy-phenyl)-2-[benzyl-(5,6-diethyl-indan-2-yl)-amino]-ethanone 2-[Benzyl-(5,6-diethyl-indan-2-yl)amino]-1-(4-benzyloxy-3-nitro-phenyl)ethanone 1-(4-Benzyloxy-3-nitro-phenyl)-2-bromo-ethanone (2.00 g) (Prepared following procedure; Hett, Robert; Fang, Qun Kevin; Gao, Yun; Hong, Yaping; Butler, Hal T.; Nie, Xiaoyi; Wald, Stephen A. *Tetrahedron Lett.* 1997, 38, 1125-1128) is dissolved in methylmethylketone (100 mL). Triethylamine (0.64 g) is added followed by benzyl-(5,6-diethyl-indan-2-yl)-amine (1.60 g). The reaction mixture is then refluxed. The reaction is shown to be complete by TLC after 3 hours. The solvent is removed in vacuo and the product is purified by flash column chromatography (silica, n-hexane/ethyl acetate 4:1). TLC (silica, n-hexane/ethyl acetate 2:1 $R_f$=0.75).

1-(3-Amino-4-benzyloxy-phenyl)-2-[benzyl-(5,6-diethyl-indan-2-yl)-amino]-ethanone is prepared from 2-[benzyl-(5,6-diethyl-indan-2-yl)-amino]-1-(4-benzyloxy-3-nitro-phenyl)-ethanone (1.50 g) by an analogous procedure to that used to prepare (R)-1-(3-Amino-4-benzyloxy-phenyl)-2-[benzyl-(5,6-diethyl-indan-2-yl)-amino]-ethanol in Example 19. The reaction is shown to be complete by TLC after 48 hours. The catalyst is filtered off and the solvent is removed in vacuo. The product is purified by flash column chromatography (silica, n-hexane/ethyl acetate 4:1). TLC (Silica, n-hexane/ethyl acetate 2:1 $R_f$=0.70).

$^1$H NMR [CDCl$_3$, 400 MHz] d 1.20 (6H, t), 1.60 (2H, broad), 2.60 (4H, q), 3.00 (4H, m), 3.90 (6H, m), 5.15 (2H, s), 6.80 (1H, d), 6.95 (2H, s), 7.30 (12H, m).

Intermediate 21

Benzyl-(4,5,6,7-tetramethyl-indan-2-yl)-amine

3-Chloro-1-(2,3,4,5-tetramethyl-phenyl-propan-1-one is prepared from 1,2,3,4-tetramethyl-benzene and 3-chloro propionyl chloride by a procedure analogous to that of Preparation 1.

$^1$H NMR (CD$_3$OD) ppm: 7.5 (1H, s); 4.2 (2H, t); 3.6 (2H, t); 2.6 (3H, s); 2.57 (3H, s); 2.52 (3H, s); 2.5 (3H, s).

4,5,6,7-Tetramethyl-indan-1-one is prepared from 3-chloro-1-(2,3,4,5-tetramethyl-phenyl)-propan-1-one by a procedure analogous to that of Preparation 2.

$^1$H NMR (CD$_3$OD) ppm: 3.2 (2H, t); 2.9 (2H, t); 2.85 (3H, s); 2.6 (3H, s); 2.55 (3H, s); 2.5 (3H, s).

4,5,6,7-Tetramethyl-indan-1,2-dione 2-oxime is prepared from 4,5,6,7-tetramethyl-indan-1-one by a procedure analogous to that of Preparation 3.

$^1$H NMR (d6-DMSO) ppm: 12.4 (1H, s), 3.65 (2H, s); 2.7 (3H, s); 2.4 (3H, s); 2.3 (6H, s).

2-Amino-4,5,6,7-tetramethyl-indan-1-one hydrochloride is prepared from 4,5,6,7-tetramethyl-indan-1,2-dione 2-oxime by a procedure analogous to that of Preparation 4.

$^1$H NMR (d6-DMSO) ppm: 9.0 (3H, bd s); 4.5 (1H, bd t); 3.7 (1H, dd); 3.2 (1H, dd); 2.8 (3H, s); 2.6 (3H, s); 2.5 (6H, 2 s).

N-(4,5,6,7-Tetramethyl-1-oxo-indan-2-yl)-benzamide

Benzoyl chloride (1.635 g) is added dropwise to 4,5,6,7-tetramethyl-indan-1,2-dione 2-oxime (2.53 g) and triethylamine (2.25 g) in anhydrous dichloromethane (60 ml) at 0° C. The reaction mixture is stirred at room temperature for 1.5 hours after which the solid product is filtered off and allowed to stir with water (150 ml), refiltered and dried. The organic filtrate is washed with 1M HCl, 10% brine, saturated sodium bicarbonate solution, 10% brine and treated with magnesium sulphate. After filtration, the solvent is removed in vacuo and the product triturated with diethyl ether, filtered and dried.

$^1$H NMR (CDCl$_3$) ppm: 7.8 (2H, d); 7.45 (1H, m), 7.4 (2H, m); 6.8 (1H, bd d); 4.6 (1H, m); 3.8 (1H, dd); 2.8 (1H, dd); 2.55 (3H, s); 2.25 (3H, s); 2.15 (6H, 2 s).

N-(1-Hydroxy-4,5,6,7-tetramethyl-indan-2-yl)-benzamide

Sodium borohydride (213 mg) is added to N-(4,5,6,7-tetramethyl-1-oxo-indan-2-yl)-benzamide (495 mg) in chloroform (20 ml) and methanol (20 ml). The reaction mixture is stirred at room temperature for 2 hours, drowned with water (50 ml) and chloroform (20 ml) added. The aqueous phase is washed with chloroform (×2) and the organic layers combined, treated with magnesium sulphate, filtered and the solvent removed in vacuo.

$^1$N NMR (CDCl$_3$) ppm: 7.65 (2H, d); 7.4 (1H, m), 7.35 (2H, m); 6.3 (1H, bd d); 5.15 (1H, d); 4.5 (1H, m); 3.7 (1H, bd s); 3.5 (1H, dd); 2.65 (1H, dd); 2.25 (3H, s); 2.15 (9H, 3 s).

N-(4,5,6,7-Tetramethyl-indan-2-yl)-benzamide is prepared from N-(1-Hydroxy-4,5,6,7-tetramethyl-indan-2-yl)-benzamide by a procedure analogous to that of Preparation 4.

$^1$H NMR (CDCl$_3$) ppm: 7.65 (2H, d); 7.4 (1H, m), 7.3 (2H, m); 6.25 (1H, bd d); 4.85 (1H, m); 3.35 (1H, dd); 2.80 (1H, dd); 2.1 (12H, 2s).

Benzyl-(4,5,6,7-tetramethyl-indan-2-yl)-amine

1M Lithium aluminium hydride (2.4 ml) in tetrahydrofuran is added dropwise to a solution of N-(4,5,6,7-tetramethyl-indan-2-yl)-benzamide (352 mg) in anhydrous THF (10 ml) under nitrogen at room temperature. The reaction mixture is allowed to stir at 50° C. for 20 hours. After 4 hours more 1M Lithium aluminium hydride (1.2 ml, 1.20 mmol) in THF is added. On cooling the reaction mixture is quenched with ice water. The aqueous phase is washed with diethyl ether (×3) and the organic layers combined, treated with magnesium sulphate, filtered and the solvent removed in vacuo.

$^1$H NMR (CDCl$_3$) ppm: 7.25 (4H, m); 7.15 (1H, m); 3.8 (2H, s); 3.55 (1H, m); 3.1 (2H, dd); 2.7 (2H, dd); 2.1 (12H, 2s).

Intermediate 22

Benzyl-(2,3,5,6,7,8-hexahydro-1H-cyclopenta[b]naphthalen-2-yl)-amine

According to the procedure of A. F. Abdel-Magid, et. al. *J. Org. Chem.* 1996, 61, 3849-3862, triethylamine (0.87 mL, 6.17 mmol) is added to a stirred suspension 2,3,5,6,7,8-hexahydro-1H-cyclopenta[b]naphthalen-2-ylamine in 1,2-dichloroethane (30 mL) under nitrogen at room temperature. Benzaldehyde (0.52 mL, 5.14 mmol) is then added followed by sodium triacetoxyborohydride (1.64 g, 7.7 mmol) and acetic acid (0.44 mL, 7.7 mmol). The reaction is stirred at room temperature for 18 hours. After diluting with dichloromethane the mixture is washed with aqueous NaOH (50 mL, 1M) followed by brine. Removal of the solvent and chromatography (silica, ethyl acetate/hexane, 2:1) affords an oil.

$^1$H-NMR (CDCl$_3$) ppm: 1.70 (m, 4H), 2.65 (m, 4H), 2.68 (dd, 2H), 3.05 (dd, 2H), 3.58 (m, 1H), 3.78 (s, 2H), 6.83 (s, 2H), 7.25 (m, 5H).

Intermediate 23

2-Methyl-indan-2-ylamine

2-Amino-2-methyl-indan-1-one

According to the procedure of Farnum et. al (*Synthesis* 1972, 191-192), water (1.35 L) is stirred at 80° C. and degassed by periodic evacuating and flushing with nitrogen (3×). K$_3$FeCN$_6$ (202 g, 615 mmol) and 2-methyl-indan-1-one (20 g, 1.37 mmol) are added. The mixture is stirred rapidly under nitrogen at 80° C. while aqueous concentrated ammonia solution (105 mL) is added over 30 minutes. Stirring is continued at 80° C. for 20 hours. When cool, the solution is made alkaline by addition of sodium hydroxide (2 g) and extracted with ethyl acetate (2×200 mL). The organic extract is concentrated to a volume of 200 ml and the product is extracted into aqueous HCl (200 mL, 1M). The acidic aqueous phase is separated, gasified with sodium hydroxide, and extracted with ethyl acetate (2×100 mL). The organic layer is separated, dried (Na$_2$SO$_4$) and the solvent removed to give an orange oil.

$^1$H-NMR (CDCl$_3$) ppm: 1.38 (s, 3H), 1.8 (br. s, 2H), 3.07 (d, 1H), 3.25 (d, 1H), 3.45 (m, 2H), 7.65 (t, 1H), 7.80 (d, 1H).

2,2,2-Trifluoro-N-(2-methyl-1-oxo-indan-2-yl)-acetamide

2-Amino-2-methyl-indan-1-one (16.4 g) in THF (100 mL) is cooled to 0° C. under nitrogen. Triethylamine (21 ml) is added followed by slow addition of trifluoroacetic anhydride (18.5 ml). The reaction is stirred at room temperature-overnight then the solvents are removed. The residue is dissolved in dichloromethane and washed with aqueous HCl followed by aqueous NaOH. The organic extract is dried (MgSO$_4$) and the solvent is removed. The product is purified by chromatography (silica, ethyl acetate) to give a cream solid.

$^1$H-NMR (CDCl$_3$) ppm: 1.52 (s, 3H), 3.44 (d, 1H), 3.55 (d, 1H), 7.05 (br.s, 1H), 7.43 (m, 2H), 7.70 (t, 1H), 7.87 (d, 1H).

2,2,2-Trifluoro-N-(2-methyl-indan-2-yl)-acetamide 2,2,2-Trifluoro-.N.-(2-methyl-1-oxo-indan-2-yl-acetamide (3.41 g) in acetic acid (25 mL) and H$_2$SO$_4$ (0.5 mL) is stirred under hydrogen in the presence of 10% Pd/C at room temperature for 18 hours. The mixture is filtered through celite and the filtrate is concentrated in vacuo. After diluting with water the mixture is extracted with diethyl ether. The organic phase is removed, washed several times with aqueous sodium bicarbonate and dried (Na$_2$SO$_4$). The solvent is removed to give an oil which solidifies.

$^1$H-NMR (CDCl$_3$) ppm: 1.55 (s, 3H, 3.05 (d, 2H), 3.28 (d, 2H), 6.28 (br.s, 1H), 7.12 (s, 4H).

2-Methyl-indane-2-ylamine

A stirred solution of 2,2,2-trifluoro-.N.-(2-methyl-indan-2-yl)-acetamide (6.70 g) and NaOH (4.0 g) in methanol (100 mL) and water (1 mL) is heated at 70° C. for 2 hours. The solvent is removed and the residue is partitioned between aqueous HCl (100 mL, 2M) and ethyl acetate (100 mL). The aqueous extract is separated, basified with aq. NaOH, and extracted with ethyl acetate. The organic phase is separated, dried (MgSO$_4$), and the solvent is removed to give an orange oil which solidifies.

$^1$H-NMR (CDCl$_3$) ppm: 1.19 (s, 3H), 1.5 (br.s, 2H), 2.65 (d, 2H), 2.79 (d, 2H), 6.97 (m, 4H).

Intermediate 24

2-Methyl-2,3,5,6,7,8-hexahydro-1H-cyclopenta[b]naphthalene-2-ylamine 1-(5,6,7,8-Tetrahydro-naphthalene-2-yl)-propan-1-one Propionyl chloride 17.5 mL) and 1,2,3,3-tetrahydronaphthalene (27.5 mL) are added slowly over 1 hour to a stirred solution of AlCl$_3$ (61.3 g) in nitromethane (200 mL) at 0° C. After stirring at room temperature for 18 hours the reaction is cautiously added to a mixture of ice and concentrated HCl. The product is extracted with ethyl acetate, washed with brine and dried (Na$_2$SO$_4$).

$^1$H-NMR (CDCl$_3$) ppm: 1.15 (t, 3H), 1.72 (m, 4H), 2.72 (m, 4H), 2.88 (q, 2H), 7.04 (d, 1H), 7.60 (m, 1H).

2-Methyl-2,3,5,6,7,8-hexahydro-cyclopenta[b]naphthalen-1-one

According to the procedure of Bhattacharya et. al (*Synth. Commun* 1996, 26, 1775-1784) a mixture of 1-(5,6,7,8-tetrahydro-naphthalen-2-yl)-propan-1-one (37.6 g), hexamethylenetetramine (44.9 g) and acetic anhydride (38.8 mL) is heated with stirring at 80° C. for 23 hours. The mixture is allowed to cool, and added slowly to a stirred mixture of ethyl acetate (200 mL) and aqueous sodium hydroxide (200 mL, 2M). The organic layer is separated, washed with aqueous HCl, brine, and dried (Na$_2$SO$_4$). The solvent is removed to give a brown oil. This is added cautiously to concentrated sulfuric acid (120 mL) and the resulting mixture is heated at 55° C. for 5 hours followed by room temperature for 18 hours. The reaction is diluted with water and extracted with dichloromethane. After drying (Na$_2$SO$_4$) the solvent is removed to give an oil. The product is purified by chromatography (silica, ethyl acetate/hexane) to give a geometrical mixture of isomers containing 2-Methyl-1,2,6,7,8,9-hexahydro-cyclopenta[.a.]naphthalene-3-one and the title compound.

$^1$H-NMR (CDCl$_3$) ppm (mixture): 1.4 (m, 3H), 1.9 (m, 4H), 2.5-3.0 (m, 6H), 3.35 (m, 1H), 7.15 (m, 1H), 7.55 (m, 1H).

2,2,2-Trifluoro-N-(2-methyl-1-oxo-2,3,5,6,7,8-hexahydro-1H-cyclo[b]naphthalen-2-yl)-acetamide The compound is prepared from an isomeric mixture, containing 2-methyl-2,3,5,6,7,8-hexahydro-cyclopenta[b]naphthalen-1-one, according to the procedure used for the preparation of 2,2,2-trifluoro-.N.-(2-methyl-1-oxo-indan-2-yl)-acetamide. The isomeric mixture of products is recrystallised from ethyl acetate/hexane to give a 4:1 mixture in favour of the title compound.

$^1$H-NMR (CDCl$_3$) ppm (major component): 155 (s, 3H), 1.85 (m, 4H), 2.87 (m, 4H), 6.88 (br.s, 1H), 7.18 (s, 1H), 7.57 (s, 1H).

TOF MS ES$^+$ m/e 310 (M+H$^+$).

2-Methyl-2,3,5,6,7,8-hexahydro-1H-cyclopenta[b]naphthalen-2-ylamine

A 4:1 mixture of geometrical isomers, containing predominantly 2,2,2-trifluoro-.N.-(2-methyl-1-oxo-2,3,5,6,7,8-hexahydro-1H-cyclopenta[b]naphthalen-2-yl)-acetamide, is hydrogenated over PD/C in acetic acid/H$_2$SO$_4$ and the products are saponified with NaOH according to the procedures described for the preparation of 2-methyl-indan-2-ylamine. The resulting product mixture is recrystallised repeatedly from hexane to give the title compound, a single isomer.

$^1$H-NMR (CDCl$_3$) ppm: 1.40 (s, 3H), 1.6 (br.s, NH$_2$), 1.75 (m, 4H), 3.75 (m, 4H), 2.78 (d, 2H), 2.94 (d, 2H), 6.93 (s, 2H).

Intermediate 25

2-Ethyl-indan-2-ylamine

2-Ethyl-indan-1-one is prepared from benzene following analogous procedures to those used for 2-methyl-2,3,5,6,7,8-hexahydro-cyclopenta[b]naphthalen-1-one.

$^1$H-NMR (CDCl$_3$) ppm: 0.97 (t, 3H), 1.50 (m, 1H), 1.90 (m, 1H), 2.55 (m, 1H), 2.75 (dd, 1H), 3.25 (q, 1H), 7.29 (t, 1H), 7.39 (d, 1H), 7.50 (t, 1H), 7.69 (d, 1H).

2-Ethyl-indan-2-ylamine is prepared from 2-ethyl-indan-1-one by procedures analogous to those used for Intermediate 23.

$^1$H-NMR (CDCl$_3$) ppm: 1.05 (t, 3H), 1.5 (br.s, NH$_2$), 2.70 (q, 2H), 2.75 (d, 2H), 3.01 (d, 2H), 7.20 (m, 4H).

Intermediate 26

2,5,6-Trimethyl-indan-2-ylamine 2,5,6-Trimethyl-indan-2-ylamine is prepared from 1,2-dimethylbenzene by procedures analogous to those used for 2-methyl-2,3,5,6,7,8-hexahydro-1H-cyclopenta[b]naphthalen-2-ylamine.

$^1$H-NMR (CDCl$_3$) ppm: 1.29 (s, 3H), 2.16 (s, 6H), 2.69 (d, 2H), 2.84 (d, 2H), 2.89 (s, 2H).

Intermediate 27

Acetic acid (R)-1-(3-amino-4-benzyloxy-phenyl)-2-[benzyl-(2-methyl-indan-2-yl)-amino]-ethyl ester (R)-2-[Benzyl-(2-methyl-indan-2-yl)-amino]-1-(4-benzyloxy-3-nitro-phenyl)-ethanol The title compound is prepared from (R)-2-(4-benzyloxy-3-nitro-phenyl)-oxirane (2.52 g) and benzyl-(2-methyl-indan-2-yl)-amine (2.20 g) by an analogous procedure to that used to prepare (S)-8-Benzyloxy-5-[2-(5,6-diethyl-indan-2-ylamino)-1-hydroxy-ethyl]-1H-quinolin-2-one in Example 19. The reaction is shown to be complete by TLC after 24 hours. The product is purified by flash column chromatography (silica, n-hexane/ethyl acetate 4:1). TLC silica, n-hexane/ethyl acetate 4:1 R$_f$=0.30).

$^1$H NMR [CDCl$_3$, 400 MHz] d 1.20 (3H, s), 2.65 (1H, m), 2.75 (1H, m), 2.90 (2H, m), 3.25 (2H, m), 3.60 (1H, d), 3.70 (1H, broad), 3.80 (1H, d of d), 4.10 (1H, d), 5.20 (2H, s), 7.00 (1H, d), 7.20 (4H, m), 7.35 (11H, m), 7.60 (1H, d).

Acetic acid (R)-2-[benzyl-(2-methyl-indan-2-yl)-amino]-1-(4-benzyloxy-3-nitro-phenyl)-ethyl ester (R)-2-[Benzyl-(2-methyl-indan-2-yl)-amino]-1-(4-benzyloxy-3-nitro-phenyl)-ethanol (2.75 g) is dissolved in pyridine (1.5 mL). Acetic anhydride (1.66 g) is added and the reaction mixture is stirred at room temperature. The reaction is shown to be complete by TLC after 18 hours. Water (10 mL) is added to quench the reaction. Ethyl acetate (250 mL) is added and the solution is washed with 1M KHSO$_4$ (3×100 mL), saturated NaHCO$_3$ (100 mL), water (100 mL) and brine (100 mL). The organic layer is dried over MgSO$_4$, filtered and the solvent is removed in vacuo. The product is not purified further. TLC (silica, n-hexane/ethyl acetate 4:1 R$_f$=0.40).

$^1$H NMR [CDCl$_3$, 400 MHz] d 1.20 (3H, s), 1.90 (3H, s), 2.80 (3H, m), 3.00 (1H, d), 3.10 (1H, m), 3.20 (1H, d) 3.75 (1H, d), 3.90 (1H, d), d), 5.20 (2H, s), 5.25 (1H, m), 6.95 (1H, d), 7.10 (4H, m), 7.30 (11H, m), 7.55 (1H, d).

Acetic acid (R)-1-(3-amino-4-benzyloxy-phenyl)-2-[benzyl-(2-methyl-indan-2-yl)-amino]-ethyl ester The title compound is prepared from acetic acid (R)-2-[benzyl-(2-methyl-indan-2-yl)amino]-1-(4-benzyloxy-3-nitro-phenyl)-ethyl ester (2.90 g) by an analogous procedure to that used to prepare (R)-1-(3-amino-4-benzyloxy-phenyl)-2-[benzyl-(5,6-diethyl-indan-2-yl)-amino]-ethanol in Example 19. The reaction is shown to be complete by TLC after 6 hours. The catalyst is filtered off and the solvent is removed in vacuo. The product is not purified further. TLC (silica, n-hexane/ethyl acetate 2:1 R$_f$=0.60).

$^1$H NMR [CDCl$_3$, 400 MHz] d 1.10 (3H, s), 1.80 (3H, s), 2.70 (3H, m), 3.05 (2H, m), 3.15 (1H, d), 3.65 (2H, broad), 3.75 (1H, d), 3.90 (1H, d), 4.95 (2H, s), 5.20 (1H, m), 6.40 (2H, m), 6.65 (1H, d), 7.20 (14H, m).

Intermediate 28

Benzyl-(2,5,6-trimethyl-indan-2-yl)-amine

N-2,5,6-Trimethyl-indan-2-yl)-benzamide

Intermediate 26 is treated with benzoyl chloride in dichloroethane/triethylamine for 1 hour. The mixture is washed with 1N HCl, then with saturated NaHCO$_3$ solution, dried (Na$_2$SO$_4$) and evaporated. The residue is triturated with ether/hexane to give white crystals.

$^1$H-NMR (CDCl$_3$) ppm: 1.60 (s, 3H), 2.18 (s, 6H), 3.02 (d, 2H), 3.30 (d, 2H), 6.17 (br.s, NH), 6.90 (s, 2H), 7.334 (m, 2H), 7.40 (m, 1H), 7.63 (d, 1H).

Benzyl-(2,5,6-trimethyl-indan-2-yl)-amine

To a solution of N-(2,5,6-trimethyl-indan-2-yl)-benzamide in THF under nitrogen is added LiAlH$_4$ and the mixture refluxed for 48 hours. Quenched at 0° C. with ice/water and extracted with ether, dried (Na$_2$SO$_4$) and solvent removed in vacuo. Purification by chromatography (silica, ethyl acetate/hexane 1:4) gives a colourless oil.

$^1$H-NMR (CDCl$_3$) ppm: 1.58 (s, 3H), 1.79 (br.s. NH), 2.40 (s, 6H), 3.00 (d, 2H), 3.20 (d, 2H), 3.99 (s, 2H), 7.15 (s, 2H), 7.37-7.53 (m, 5H).

Intermediate 29

Acetic acid (R)-1-(3-amino-4-benzyloxy-phenyl)-2-[benzyl-(2,5,6-trimethyl-indan-2-yl)-amino]-ethyl ester (R)-1-(4-Benzyloxy-3-nitro-phenyl)-2-[benzyl-(2,5,6-trimethyl-indan-2-yl)-amino]-ethanol A mixture of 2-(4-methyl-3-nitro-phenyl)-oxirane and benzyl-(2,5,6-trimethyl-indan-2-yl)-amine is heated at 110° C. for 48 hours. The material is used without further purification.
ES$^+$ MS m/e 538 (MH$^+$)

Acetic acid (R)-1-(4-benzyloxy-3-nitro-phenyl)-2-[benzyl-(2,5,6-trimethyl-indan-2-yl)-amino]-ethyl ester To a solution of (R)-1-(4-Benzyloxy-3-nitro-phenyl)-2-[benzyl-(2,5,6-trimethyl-indan-2-yl)-amino]-ethanol in pyridine is added acetic anhydride and the mixture stirred for 18 hours. The reaction mixture is quenched with water and after addition of ethyl acetate washed twice with aqueous KHSO$_4$ solution, twice with aqueous NaHCO$_3$ and once with brine. The product is purified by chromatography (silica, ethyl acetate/hexane 1:4). ES$^+$ MS m/e 579 (MH$^+$).

Acetic acid (R)-1-(3-amino-4-benzyloxy-phenyl)-2-[benzyl-(2,5,6-trimethyl-indan-2-yl)-amino]-ethyl ester Acetic acid (R)-1-(4-benzyloxy-3-nitro-phenyl)-2-[benzyl-(2,5,6-trimethyl-indan-2-yl)-amino]-ethyl ester in a mixture of THF and toluene is stirred under hydrogen in the presence of PrO$_2$ at room temperature for 15 hours. The mixture is filtered through celite and the filtrate is concentrated in vacuo. ES$^+$ MS m/e 549 (MH$^+$).

Intermediate 30

5,6-Diethyl-2-methyl-indan-2-ylamine

N-(5-Acetyl-2-methyl-indan-2-yl)-benzamide

Aluminium chloride (3.7 g) is dissolved in nitromethane (12 ml) under nitrogen followed by N-(2-methyl-indan-2-yl)-benzamide (3.0 g) at 0° C. Acetyl chloride (0.85 ml) is added dropwise over 30 minutes. After 4 hours at room temperature the mixture is quenched with ice and concentrated HCl, extracted with DCM. The organic layers are washed with dilute HCl and brine. Evaporation of the solvent yielded the desired product. ES$^+$ MS m/e 294 (MH$^+$)

N-(5-Ethyl-2-methyl-indan-2-yl)-benzamide

A solution of N-(5-acetyl-2-methyl-indan-2-yl)-benzamide (3.4 g) in ethanol (200 ml) and conc. HCl (2 ml) is stirred under hydrogen in the presence of 10% Pd/C at room temperature for 48 hours. The mixture is filtered through celite and the filtrate is concentrated in vacuo to give the title compound.

$^1$H-NMR (CDCl$_3$) ppm: 1.20 (t, 3H), 1.60 (s, 3H), 2.55 (q, 2H), 3.05 (d, 2H), 3.35 (d, 2H), 6.35 (br.s, NH), 6.90-7.10 (m, 3H), 7.39 (d, 2H), 7.65 (s, 2H)

N-(5-Acetyl-6-ethyl-2-methyl-indan-2-yl)benzamide is prepared from N-(5-ethyl-2-methyl-indan-2-yl)-benzamide (2.6 g) following the procedure used to prepare N-(5-acetyl-2-methyl-indan-2-yl)-benzamide. The product is purified by chromatography (silica, hexane/ethyl acetate, 4:1) to give the title compound. ES$^+$ MS m/e 322 (MH$^+$)

N-(5,6-Diethyl-2-methyl-indan-2-yl)-benzamide is prepared from N-(5-acetyl-6-ethyl-2-methyl-indan-2-yl)-benzamide (1.1 g) following the procedure used to prepare N-(5-ethyl-2-methyl-indan-2-yl)-benzamide. ES$^+$ MS m/e 308 (MH$^+$)

Benzyl-(5,6-diethyl-2-methyl-indan-2-yl)-amine is prepared from N-(5,6-diethyl-2-methyl-indan-2-yl)-benzamide by an analogous procedure to that used to prepare benzyl-(5,6-diethyl-indan-2-yl)-amine in Intermediate 18. ES$^+$ MS m/e 294 (MH$^+$)

5,6-Diethyl-2-methyl-indan-2-ylamine

A solution of benzyl-(5,6-diethyl-2-methyl-indan-2-yl)-amine (0.48 g) in methanol (10 ml) is stirred under an atmosphere of hydrogen in the presence of 10% Pd/C at room temperature for 18 hours. The mixture is filtered through celite and the filtrate is concentrated in vacuo to give the title compound. ES$^+$ MS m/e 204 (MH$^+$)

EXAMPLE 1

(a) (R)-8-Benzyloxy-5-[2-(4,7-dimethoxy-indan-2-ylamino)-1-hydroxy-ethyl]-1H-quinolin-2-one (R)-8-Benzyloxy-5-oxiranylcarbostyril (100 mg, 0.34 mmol), prepared from literature procedure (Beeley, Lee James; Dean, David Kenneth, PCT Int. Appl. WO 9525104) and 4,7-dimethoxy-indman-2-ylamine (66 mg, 0.34 mmol) prepared from literature procedure (Sindelar, R. D.; Mott, J.; Barfknect, C. F.; Arneric, 5. P.; Flynn, J. R.; Long, J. P.; Bhatnagar, R. K. J. Med. Chem. (1982), 25(7), 2858-64), are dissolved in toluene (1 mL). The reaction mixture was heated to 110° C. and the solvent is allowed to evaporate. The residue is then stirred at 110° C. for 4 hours. The reaction is shown to be complete by TLC. The product is purified by flash column chromatography (silica, dichloromethane/methanol 20:1).

TLC (silica, dichloromethane/methanol 25:1 R$_f$=0.10).
ES+ MS m/e 487 (MH$^+$).

(b) (R)-8-hydroxy5-[2-(4,7-Dimethoxy-indan-2-ylamino)-1-hydroxy-ethyl]-1H-quinolin-2-one hydrochloride (R)-8-Benzyloxy-5-[2-(4,7-dimethoxy-indan-2-ylamino)-1-hydroxy-ethyl]-1H-quinolin-2-one (37 mg, 0.08 mmol) is dissolved in methanol (10 mL) and the compound is deprotected by adding a catalytic amount of 10% palladium on charcoal and placing the solution under an atmosphere of hydrogen. The reaction is shown to be complete by TLC after 4 hours. The catalyst is filtered off, 1M HCl/diethyl ether (1.1 equivalent) is added and the solvent is removed in vacuo.

TLC (silica, dichloromethane/methanol 10:1 R$_f$=0.15).
ES+ MS m/e 397 (MH$^+$).

Other compounds of formula I are prepared from (R)-8-benzyloxy-5-oxiranylcarbostyril ((R)-2-(4-benzyloxy-3-nitrophenyl)-oxirange (Intermediate 15) in Example 11) and the appropriate compound of formula XVII by procedures analogous to Example 1. These compounds, in which R$^1$ is OH, R$^2$ and R$^3$ are H, Ar is a group of formula III in which R$^{29}$, R$^{30}$ and R$^{31}$ are H (except in Example 11, where Ar is a group of formula XV in which R$^{13}$ is H) and n is 1 (except in Example 9 where n is 2) are shown in the following table.

| Example | R$^4$ | R$^5$ | R$^6$ | R$^7$ | ES + MS m/e (MH$^+$) |
|---|---|---|---|---|---|
| 2 | H | CH$_3$CH$_2$ | CH$_3$CH$_2$ | H | 393 |
| 3 | H | CH$_3$ | CH$_3$ | H | 365 |
| 4 | CH$_3$CH$_2$ | H | H | CH$_3$CH$_2$ | 393 |
| 5 | H | —(CH$_2$)$_4$— | | H | 391 |
| 6 | H | —O(CH$_2$)$_2$O— | | H | 395 |
| 7 | H | CH$_3$(CH$_2$)$_3$ | CH$_3$(CH$_2$)$_3$ | H | 449 |
| 8 | H | CH$_3$(CH$_2$)$_2$ | CH$_3$(CH$_2$)$_2$ | H | 421 |
| 9 | H | H | H | H | 365 |
| 10 | H | CH$_3$OCH$_2$ | CH$_3$OCH$_2$ | H | |
| 11 | H | CH$_3$CH$_2$ | CH$_3$CH$_2$ | H | 341 |

Example 10: $^1$H-NMR (d$_4$-MeOH) ppm: 2.78 (2H, m), 2.9 (2H, m), 3.15 (2H, m), 3.28 (6H, s), 3.7 (1H, m), 4.55 (1H, br s), 5.15 (1H, m), 6.58 (1H, d), 6.9 (1H, d), 7.11 (2H, s), 7.15 (1H, s), 8.25 (1H, s).

EXAMPLE 12

8-Hydroxy-5-[1-hydroxy-2-(indan-2-ylamino)-ethyl]-1H-quinolin-2-one

Intermediate 10 (18 mg, 0.054 mmol) is dissolved in methanol (2 ml) and cooled on ice. Sodium borohydride (6 mg, 0.12 mmol) is added over 2 hours. Concentrated HCl is then added until pH reaches 1, and the reaction mixture filtered. The filtrate is washed with methanol. The combined liquid phases are evaporated and redissolved in methanol twice. After removal of the methanol in vacuo, the residue is redissolved in water and the pH brought to 12 with 1N KOH. The solvent is removed in vacuo and the residue coevaporated twice with toluene. The residue is purified by flash chromatography (silica, CH$_2$Cl$_2$/methanol 8:2). ES+ MS m/e 337 (MH+).

EXAMPLE 13

5-[2-(5,6-Dimethyl-indan-2-ylamino)-1-hydroxy-ethyl]-8-hydroxy-1H-quinolin-2-one This compound is prepared from Intermediate 11 by a procedure analogous to that of Example 12. ES+MS m/e 397 (MH$^+$)

EXAMPLE 14

5-[2-(5,6-Diethyl-indan-2-ylamino)-1-hydroxy-ethyl]-8-hydroxy-3-methyl-1H-quinolin-2-one This is prepared from Intermediate 13 (21 mg) by the hydrogenation procedure for removal of the benzyl group used in Example 1.

$^1$H-NMR (d4-CH$_3$OH) ppm 1.11 (t, 6H), 2.11 (s, 3H), 2.58 (q, 4H); 3.01-3.37 (m, 6H), 4.10-4.16 (m, 1H), 5.31-5.38 (m, 1H), 6.91 (d, 1H), 7.00 (s, 2H), 7.21 (d, 1H), 8.13 (s, 1H).

EXAMPLE 15

(a) 5-[2-(5,6-Diethyl-indan-2-ylamino)-1-hydroxy-ethyl]-8-methoxymethoxy-6-methyl-1H-quinolin-2-one This is obtained from Intermediate 14 (20 mg) and 5,6-diethyl-indan-2-ylamine (72 mg) according to the procedure used for preparation of Intermediate 13.

$^1$H-NMR (CDCl$_3$) ppm: 1.14 (t, 6H), 2.30 (s, 3H), 2.51 (q, 4H), 2.64-3.16 (m, 6H), 3.41 (s, 3H), 3.60-3.68 (m, 1H), 5.18-5.25 (m, 3H), 6.50 (d, 1H), 7.89-7.94 (m, 3H), 8.68 (d, 2H), 9.15 (s, br, 1H).

(b) 5-[2-(5,6-Diethyl-indan-2-ylamino)-1-hydroxy-ethyl]8-hydroxy-6-methyl-1H-quinolin-2-one 3N Hydrochloric acid (1 mL) is added to a solution of 5-[2-(5,6-Diethyl-indan-2-ylamino)-1-hydroxy-ethyl]-8- methoxymethoxy-6-methyl-1H-quinolin-2-one (12 mg) in isopropanol (1 mL) and tetrahydrofuran (1 mL) at room temperature and the reaction mixture heated for 18 hours at 40° C. The solvent is removed in vacuo, and the product purified by preparative scale HPLC on a C8 column, eluting with a water/acetonitrile/trifluoroacetic acid gradient.

$^{13}$C-NMR (d4-CH$_3$OH) ppm: 15.97, 20.09, 26.34, 36.87, 51.75, 59.72, 67.33, 118.41, 119.12, 121.21, 125.45, 126.11, 128.60, 133.35, 137.52, 137.55, 142.32, 142.50, 145.69, 163.24.

EXAMPLE 16

8-hydroxy-5-[2-(5,6-diethyl-indan-2-ylamino)-1-hydroxy-ethyl]3,4-dihydro-1H-quinolin-2-one Hydrogenation of a methanol/ethanol solution of 8-hydroxy-5-([2-(5,6-diethyl-indan-2-ylamino)-1-hydroxy-ethyl]-1H-quinolin-2-one with a 10% palladium on carbon catalyst at 30° C. for 48 hours under one atmosphere of hydrogen gives the title compound after filtration and evaporation. Further purification is achieved via preparative HPLC (column: Phenomenex Luna 10 μm 150 mm×500 mm, eluent: gradient from 10% to 95% acetonitrile in water containing 0.1% trifluoroacetic acid, UV detection at 254 nm).

$^{13}$C-NMR (d6-DMSO) ppm: 15.77, 21.42, 25.01, 30.37, 37.73, 37.83, 53.88, 58.58, 67.37, 113.28, 120.21, 122.08, 124.31, 124.34, 131.01, 138.46, 138.52, 139.58, 143.12, 169.44.

EXAMPLE 17

(a) Acetic acid (R)-1-(4-benzyloxy-3-formylamino-phenyl)-2-[benzyl-(2,5,6-trimethyl-indan-2-yl)-amino]-ethyl ester To Intermediate 29 in toluene/THF is slowly added an aged mixture of formic acid and acetic anhydride and the reaction is stirred for 5 hours at room temperature. Ethyl acetate is added and washed with saturated NaHCO$_3$ solution. Purification by chromatography (silica, ethyl acetate/hexane 1:2) and trituration with ether gave off-white crystals. ES$^+$ MS m/e 577 (MH$^+$)

(b) N-(2-Benzyloxy-5-[(R)-2-[benzyl-(2,5,6-trimethyl-indan-2-yl)-amino]-1-hydroxy-ethyl]phenyl)-formamide The product of Example 17(a) is suspended in ethanol and a catalytic amount of NaOCH$_3$ in methanol is added. After two hours at 70° C. the solvent is removed and the residue purified by chromatography (silica, ethyl acetate/hexane 2:3) to give white crystals, ES$^+$ MS m/e 535 (MH$^+$)

(c) N-[2-Hydroxy-5-[(R)-1-hydroxy-2-(2,5,6-trimethyl-indan-2-ylamino)-ethyl]-phenyl]-formamide is prepared from the product of example 17(b) by a procedure analogous to that of Example 34(c). ES$^+$ MS m/e 355 (MH$^+$)

EXAMPLE 18

(a) 8-Benzylamino-5-[(R)-2-(5,6-diethyl-2-methyl-indan-2-ylamino)-1-hydroxy-ethyl]-1H-quinolin-2-one A mixture of 5,6-diethyl-2-methyl-indan-2-ylamine (0.28 g) and 8-benzyloxy-5-oxiranyl-1H-quinolin-2-one (0.42 g) in n-butanol (0.7 ml) is placed in a Prolabo microwave oven for 75 minutes, at 100° C. The product is purified by chromatography (silica, DCM/ethanol, 5:1) to give the desired product. ES$^+$ MS m/e 497 (MH$^+$)

(b) 5-[(R)-2-(5,6-Diethyl-2-methyl-indan-2-ylamino)-1-hydroxy-ethyl]-8-hydroxy-1H-quinolin-2-one A solution of the product of Example 18(a) (0.20 g) in methanol (20 ml) is stirred under an atmosphere of hydrogen in the presence of 10% Pd/C at room temperature for 2 hours. The mixture is filtered through celite and the filtrate is concentrated in vacuo. Trituration with diethyl ether gave the desired product ES$^+$ MS m/e 407 (MH$^+$)

EXAMPLE 19

(a) (S)-8-Benzyloxy-5-[2-(5,6-diethyl-indan-2-ylamino)-1-hydroxy-ethyl]-1H-quinolin-2-one is prepared from Intermediate 16 (152 mg) and Intermediate 1 (100 mg) using a procedure analogous to that of Example 1(a). TLC (silica, dichloromethane/methanol 10:1 R$_f$=0.25).

(b) (S)-5-[2-(5,6-Diethyl-indan-2-ylamino)-1-hydroxy-ethyl]-8-hydroxy-1H-quinolin-2-one hydrochloride is prepared from the product of Example 19(a) by a procedure analogous to that of Example 1(b). TLC (silica, dichloromethane/methanol 10:1 R$_f$=0.05).

EXAMPLE 20

(a) 8-Benzyloxy-5-[(R)-1-hydroxy-2-(6,7,8,9-tetrahydro-5H-benzocyclohepten-7-ylamino)-ethyl]-1H-quinolin-2-one is prepared from (R)-8-benzyloxy-5-oxiranylcarbostyril (203 mg) and Intermediate 17 (110 mg) by a procedure analogous to that of Example 1(a). TLC (silica, dichloromethane/methanol 10:1 R$_f$=0.30).

(b) S—[(R)-1-Hydroxy-2-(6,7,8,9-tetrahydro-5H-benzo-cyclohepten-7-ylamino)-ethyl]-8-hydroxy-1H-quinolin-2-one hydrochloride is prepared from the product of Example 20(a) by a procedure analogous to that of Example 1(b). TLC (silica, dichloromethane/methanol 10:1 R$_f$=0.05).

EXAMPLE 21

(a) (R)-8-benzyloxy-5-[(S)-2-[benzyl-(5,6-diethyl-indan-2-yl)-amino]-1-hydroxy-ethyl]-1H-quinolin-2-one A solution of (R)-8-benzyloxy-5-oxiranylcarbostyril (5.00 g) and 2-amino-5,6-diethylindan (3.87 g) in n-butanol is heated for 4 hours at 110° C. After cooling to room temperature toluene (100 ml) is added and the organic phase is washed with water (3×25 ml), loaded onto a silica gel chromatography column and eluted with toluene followed by a mixture of toluene:ethanol:ethyl acetate:conc. ammonia (45:10:45:2) to give the title compound.

(b) (R)-5-[2-(5,6-diethyl-indan-2-ylamino)-1-hydroxy-ethyl]-8-hydroxy-1H-quinolin-2-one maleate (R)-8-benzyloxy-5-[2-(5,6-diethyl-indan-2-ylamino)-1-hydroxy-ethyl]-1H-quinolin-2-one (360 mg) is dissolved in methanol (10 mL) and the compound is deprotected by adding a catalytic amount of 10% palladium on charcoal and placing the solution under an atmosphere of hydrogen. The reaction is shown to be complete by TLC after 4 hours. The catalyst is filtered off and the solvent is removed in vacuo. The product is taken up into isopropanol and a solution of maleic acid in isopropanol added. The title compound is obtained after recrystallisation from ethanol. TLC (silica, dichloromethane/methanol 10:1 $R_f$=0.05). ES+ MS m/e 393 (MH$^+$).

EXAMPLE 22

(a) N-(5-[(R)-2-[Benzyl-(5,6-diethyl-indan-2-yl)-amino]-1-hydroxy-ethyl]-2-benzyloxy-phenyl)-formamide is prepared from Intermediate 19 (1.00 g), formic acid (155 mg) and acetic anhydride (226 mg) using a procedure analogous to that of Example 21(a). TLC (silica, n-hexane/ethyl acetate 2:1 $R_f$=0.20).

(b) N-(5-[(R)-2-(5,6-Diethyl-indan-2-ylamino)-1-hydroxy-ethyl]-2-hydroxy-phenyl)-formamide is prepared from the product of Example 22(a) by a procedure analogous to that of Example 1(b). TLC (silica, n-hexane/ethyl acetate 2:1 $R_f$=0.05).

EXAMPLE 23

(a) (R)-2-[Benzyl-(5,6-diethyl-indan-2-yl)-amino]-1-(4-benzyloxy-3-dimethylamino-phenyl)-ethanol Intermediate 19 (0.37 g) is dissolved in CH$_3$OH (50 ml) and formaldehyde, 37% in water (5 mL), dissolved m warns (10 mL), is added. A catalytic amount of PtO$_2$ is added and the solution is stored under an atmosphere of H$_2$. The reaction is shown to be complete by TLC after 24 hours. The catalyst is filtered off, the solvent is removed in vacuo and the residue is partitioned between ethyl acetate (100 mL) and water (100 mL). The organic layer is dried over MgSO$_4$, filtered and the solvent is removed in vacuo. The product is purified by flash column chromatography (silica, n-hexane/ethyl acetate 4:1). TLC (silica, n-hexane/ethyl acetate 2:1 $R_f$=0.65).

(b) 4-[(R)-2-(5,6-Diethyl-indan-2-ylamino)-1-hydroxy-ethyl]-2-dimethylamino-phenol hydrochloride is prepared from the product of Example 23(a) by a procedure analogous to that of Example 1(b).

$^1$H NMR [DMSO, 400 MHz] δ1.10 (6H, t), 2.55 (4H, q), 3.05 (2H, m), 3.10 (6H, s), 3.20 (4H, m), 4.00 (1H, m), 4.95 (1H, m), 7.00 (2H, s), 7.15 (1H, d), 7.35 (1H, d), 7.80 (1H, s), 9.20 (1H, broad), 9.75 (1H, broad), 11.40 (1H, broad).

EXAMPLE 24

(a) (R)-2-[benzyl-(5,6-diethyl-indan-2-yl)-amino]-1-(4-benzyloxy-3-methylamino-phenyl)-ethanol The product of Example 22 (260 mg) is dissolved in dioxan (20 mL). Sodium borohydride (90 mg) is added followed by the dropwise addition of acetic anhydride (142 mg). The reaction mixture is stirred at 90° C. The reaction is shown to be complete by TLC after 4 hours. The solvent is removed in vacuo and the residue is partitioned between ethyl acetate (100 mL) and water (100 mL). The organic layer is dried over MgSO$_4$, filtered and the solvent is removed in vacuo. The product is purified by flash column chromatography (silica, n-hexane/ethyl acetate 4:1). TLC (silica, n-hexane/ethyl acetate 2:1 $R_f$=0.65).

(b) 4-[(R)-2-(5,6-Diethyl-indan-2-ylamino)-1-hydroxy-ethyl]-2-methylamino-phenol hydrochloride is prepared from the product of Example 24(a) by a procedure analogous to that of Example 1(b).

$^1$H NMR [DMSO, 400 MHz] δ1.10 (6H, t), 2.55 (4H, q), 2.85 (3H, s), 3.10 (6H, m), 4.00 (1H, m), 4.90 (1H, m), 7.00 (3H, m), 7.15 (1H, m), 7.40 (1H, m), 9.10 (1H, broad), 9.60 (1H, broad), 10.80 (1H, broad).

EXAMPLE 25

(a) N-(5-[[Benzyl-(5,6-diethyl-indan-2-yl)-amino]-acetyl]-2-benzyloxy-phenyl)-methanesulfonamide Intermediate 20 (240 mg) is dissolved in dichloromethane (10 mL). Triethylamine (56 mg) is added followed by methanesulfonyl chloride (58 mg). The reaction mixture is stirred at room temperature. The reaction is shown to be complete by TLC after 24 hours. The solvent is removed in vacuo and the product is purified by flash column chromatography (silica, n-hexane/ethyl acetate 4:1). TLC (silica, n-hexane/ethyl acetate 2:1 $R_f$=0.40).

(b) N-(5-[2-[Benzyl-(5,6-diethyl-indan-2-yl)-amino]-1-hydroxy-ethyl]-2-benzyloxy-phenyl)-methanesulfonamide The product of Example 25(a) (120 mg) is dissolved in ethanol (10 mL). Sodium borohydride (9 mg) is added and the reaction mixture is stirred at room temperature. The reaction is shown to be complete by TLC after 3 hours. The reaction mixture is quenched with 2M HCl (1 mL), the solvent is removed in vacuo and the residue is partitioned between ethyl acetate (50 mL) and saturated NaHCO$_3$ (50 mL). The organic layer is dried over MgSO$_4$, filtered and the solvent is removed in vacuo. The product is not purified further. TLC (silica, n-hexane/ethyl acetate 2:1 $R_f$=0.45).

(c) N-[5-[2-(5,6-Diethyl-indan-2-ylamino)-1-hydroxy-ethyl]-2-hydroxy-phenyl]-methanesulfonamide hydrochloride is prepared from the product of Example 25(b) by a procedure analogous to that of Example 1(b).

$^1$H NMR [CDCl$_3$, 400 MHz] δ1.15 (6H, t), 2.55 (4H, q) 2.95 (3H, s), 3.10 (6H, m), 4.00 (1H, m), 4.85 (1H, m), 6.10 (1H, broad), 6.90 (2H, d), 7.00 (2H, s), 7.10 (1H, d of d), 7.25 (1H, d), 8.75 (1H, s), 8.95 (1H, broad), 9.25 (1H, broad), 10.00 (1H, s).

EXAMPLE 26

(a) (R)-8-Benzyloxy-5-[(S)-2-[benzyl-(4,5,6,7-tetramethyl-indan-2-yl)-amino]-1-hydroxy-ethyl]-1H-quinolin-2-one (R)-8-Benzyloxy-5-oxiranylcarbostyril (204 mg) and Intermediate 21 (194 mg) are dissolved in n-butanol (0.5 ml) under nitrogen. The reaction mixture is heated at 110° C. for 22 hours. On cooling the solvent is removed in vacuo. The product is purified by flash column (b) (R)-8-Hydroxy-5-[(S)-1-hydroxy-2-(4,5,6,7-tetramethyl-indan-2-ylamino)-ethyl]-1H-quinolin-2-one is prepared from the product of Example 26(a) by a procedure analogous to that of Example 1(b).

$^1$H NMR (CD$_2$OD) ppm: 8.55 (1H, d); 7.5 (1H, d); 7.25 (1H, d); 6.9 (1H, d); 5.6 (1H, m); 4.3 (1H, m); 3.7 (2H, q); 3.6 (2H, dd); 3.3 (2H, dd); 2.4 (12H, s)

EXAMPLE 27

(a) 8-Benzyloxy-5-[(R)-1-hydroxy-2-(2-methyl-indan-2-ylamino)-ethyl]-1H-quinolin-2-one A mixture of 8-benzyloxy-5-(R)-oxiranyl-1H-quinolin-2-one (500 mg) and 2-methyl-indan-2-ylamine (276 mg) in n-butanol (1 mL) is subjected to microwave irradiation, using a Prolabo Synthewave 402 instrument, for 90 minutes at 110° C. The residue is absorbed on silica and the product is purified by flash chromatography (silica, chloroform/ethanol 4:1).

$^1$H NMR (CDCl$_3$) ppm: 1.30 (s, 3H), 2.65 (s, 1H), 2.95 (dd, 2H), 3.07 (m, 3H), 5.15 (m, 1H), 5.18 (s, 2H), 6.66 (d, 1H), 7.17 (m, 4H), 7.26 (d, 1H), 7.45 (m, 5H), 8.07 (d, 1H), 8.8-9.5 (br.d, 1H)

(b) 8-Hydroxy-5-[(R)-1-hydroxy-2-(2-methyl-indan-2-ylamino)-ethyl]-1H-quinolin-2-one The product of Example 27(a) (100 mg, 0.22 mmol) is dissolved in methanol (20 ml) and is deprotected by adding a catalytic amount of 10% palladium on charcoal and stirring under an atmosphere of hydrogen for 1 hour. The catalyst is removed and the solvent is evaporated to give a yellow solid.

$^1$H NMR (d$_4$-CH$_3$OH) ppm: 1.20 (s, 3H), 2.75 (m, 4H), 2.95 (d, 2H), 5.03 (m, 1H), 6.60 (d, 1H), 6.82 (d, 1H), 7.0 (m, 4H), 7.08 (d, 1H), 8.20 (d, 1H).

EXAMPLE 28

5-[2-(5,6-Diethyl-indan-2-ylamino)-ethyl]-8-hydroxy-1H-quinolin-2-one

This compound is prepared from the product of Example 2 according to the procedure of Temple et al, J. Med. Chem., 19, 626-633 (1976).

$^1$H-NMR (d$_4$-CH$_3$OH) ppm: 1.08 (t, 3H), 2.55 (q, 4H), 2.96 (dd, 2H), 3.18 (m, 4H), 3.28 (dd, 2H), 3.99 (m, 1H), 6.60 (d, 1H), 6.90 (d, 1H), 6.97 (d, 1H), 6.00 (s, 2H), 8.07 (d, 1H).

EXAMPLE 29

(a) 8-Benzyloxy-5-[(R)-1-hydroxy-2-(2-methyl-2,3,5,6,7,8-hexahydro-1H-cyclopenta[b]naphthalen-2-ylamino) ethyl]-1H-quinolin-2-one is prepared from 8-benzyloxy-5-(R)-oxiranyl-1H-quinolin-2-one (220 mg) and Intermediate 24 (150 mg) by procedures analogous to those of Example 27(a).

$^1$H NMR (CDCl$_3$) ppm: 1.37 (s, 1H), 1.78 (m, 4H), 2.1 (br.s, 2H), 2.72 (m, 5H), 2.80 (dd, 2H), 2.95 (m, 3H), 5.08 (m, 1H), 5.17 (s, 2H), 6.65 (d, 1H), 6.88 (s, 2H), 7.02 (d, 2H), 7.26 (d, 1H), 7.4 (m, 5H), 8.05 (d, 1H).

(b) 8-Hydroxy-5-[(R)-1-hydroxy-2-(2-methyl-2,3,5,6,7,8-hexahydro-1H-cyclopenta[b]naphthalen-2-ylamino)-ethyl]-1H-quinolin-2-one is prepared by hydrogenation of the product of Example 29(a) using a procedure analogous to that of Example 27(b). The product is purified by HPLC (H$_2$O, CH$_3$CN, CF$_3$COOH, gradient elution).

$^1$H NMR (d$_4$-CH$_3$OH) ppm (TFA salt): 1.65 (s, 3H), 1.85 (m, 4H), 2.85 (m, 4H), 3.15 (m, 2H), 3.4 (m, 4H), 5.48 (t, 1H), 6.83 (d, 1H), 7.03 (s, 1H), 7.15 (d, 1H), 7.45 (d, 1H), 8.40 (d, 1H).

EXAMPLE 30

(a) 5-[(S)-2-[Benzyl(2,3,5,6,7,8-hexahydro-1H-cyclopenta[b]naphthalen-2-yl)-amino]-1-hydroxy-ethyl]-8-benzyloxy-1H-quinolin-2-one A mixture of Intermediate 16 (150 mg) and benzyl-(2,3,5,6,7,8-hexahydro-1H-cyclopenta[b]naphthalen-2-yl)-amine (142 mg) in toluene (1 mL) is heated at 80° C. for 36 hours. The residue is purified by chromatography (silica, CHCl$_3$/EtOH, 20:1) to give a yellow foam.

$^1$H NMR (CDCl$_3$) ppm: 1.77 (m, 4H), 2.72 (m, 6H), 3.01 (m, 4H), 3.70 (d, 1H), 3.88 (d, 1H), 4.82 (m, 1H), 5.15 (s, 2H), 6.50 (d, 1H), 6.8-8 (m, 13H), 9.05 (br.s, 1H)

(b) 5-[(S)-2-(2,3,5,6,7,8-Hexahydro-1H-cyclopenta[b]naphthalen-2-ylamine)-1-hydroxyethyl]-8-hydroxy-1H-quinolin-2-one A solution of the product of Example 30(a) (150 mg) in methanol (20 mL) is stirred under an atmosphere of hydrogen in the presence of 10% Pd/C (20 mg) at room temperature for 5 hours. The reaction is filtered and the product is purified by chromatography (silica, CHCl$_3$/EtOH, 20:1) followed by crystallisation (CH$_3$OH).

$^1$H-NMR (d$_4$-CH$_3$OH) ppm: 1.65 (m, 4H), 2.57 (m, 4H), 2.86 (dd, 2H), 3.1 (m, 4H), 3.82 (m, 1H), 5.25 (m, 1H), 6.55 (d, 1H), 6.78 (s, 2H), 6.91 (d, 1H), 7.19 (d, 1H), 8.27 (d, 1H).

EXAMPLE 31

(a) Acetic acid (R)-2-[benzyl-(2-methyl-indan-2-yl)-amino]-1-(4-benzyloxy-3-methanesulfonylamino-phenyl)-ethyl ester is prepared from Intermediate 27 (476 mg), triethylamine (231 mg) and methanesulfonyl chloride (210 mg) by a procedure analogous to that of Example 25(b). TLC (silica, n-hexane/ethyl acetate 2:1 R$_f$=0.45).

(b) N-(5-[(R)-2-[Benzyl-(2-methyl-indan-2-yl)-amino]-1-hydroxy-ethyl]-2-benzyloxy-phenyl)-methanesulfonamide The product of Example 31(a) (200 mg) is dissolved in CH$_3$OH (8 mL), K$_2$CO$_3$ (138 mg) is added followed by the dropwise addition of water (2 mL). The reaction mixture is stirred at room temperature. The reaction is shown to be complete by TLC after 24 hours. Ethyl acetate (100 mL) is added and the solution is washed with water (50 mL) and brine (50 mL). The organic layer is dried over MgSO$_4$, filtered and the solvent is removed in vacuo. The product is purified by flash column chromatography (silica, n-hexane/ethyl acetate 3:1). TLC (silica, n-hexane/ethyl acetate 2:1 R$_f$=0.35).

(c) N-[2-Hydroxy-5-[(R)-1-hydroxy-2-(2-methyl-indan-2-ylamino)-ethyl]-phenyl]-methanesulfonamide) is prepared from the product of Example 31(b) by a procedure analogous to that of Example 1(b). TLC (silica, dichloromethane/methanol 10:1 R$_f$=0.10).

EXAMPLE 32

(a) Acetic acid (R)-2-[benzyl-(2-methyl-indan-2-yl)-amino]-1-(4-benzyloxy-3-ethanesulfonylamino-phenyl)-ethyl ester is prepared from Intermediate 27, triethylamine (242 mg) and ethanesulfonyl chloride (247 mg) by a procedure analogous to that of Example 25(b). TLC (silica, n-hexane/ethyl acetate 2:1 R$_f$=0.05).

(b) Ethanesulfonic acid (5-[(R)-2-[benzyl-(2-methyl-indan-2-yl)-amino]-1-hydroxy-ethyl]-2-benzyloxy-phenyl)-amide is prepared from the product of Example 32(a) by a procedure analogous to that in Example 31(b). TLC (silica, n-hexane/ethyl acetate 2:1 R$_f$=0.40).

(c) Ethanesulfonic acid [2-hydroxy-5-[(R)-1-hydroxy-2-(2-methyl-indan-2-ylamino)-ethyl]-phenyl]-amide is prepared from the product of Example 32(b) by a procedure analogous to that of Example 1(b). TLC (silica, dichloromethane/methanol 10:1 R$_f$=0.10).

EXAMPLE 33

(a) Acetic acid (R)-2-[benzyl-(2-methyl-indan-2-yl)-amino]-1-[4-benzyloxy-3-(propane-1-sulfonylamino)-phenyl]-ethyl ester) is prepared from Intermediate 27 (525 mg), triethylamine (255 mg) and 1-propanesulfonyl chloride (288 mg) by a procedure analogous to that of Example 25(a). TLC (silica, n-hexane/ethyl acetate 4:1 $R_f$=0.25).

(b) Propane-1-sulfonic acid (5-[(R)-2-[benzyl-(2-methyl-indan-2-yl)-amino]-1-hydroxy-ethyl]-2-benzyloxy-phenyl)-amide is prepared from the product of Example 33(a) by a procedure analogous to of Example 31(b). TLC (silica, n-hexane/ethyl acetate 4:1 $R_f$=0.15).

(c) Propane-1-sulfonic acid (2-hydroxy-5-[(R)-1-hydroxy-2-(2-methyl-indan-2-ylamino)-ethyl]-phenyl)-amide is prepared from the product of Example 33(b) by a procedure analogous to that of Example 1(b). TLC (silica, dichloromethane/methane 10:1 $R_f$=0.05).

EXAMPLE 34

(a) (N-[2-Benzyloxy-5-[(2-ethyl-indan-2-ylamino)-acetyl]-phenyl]-methanesulfonamide A mixture of 2-ethyl-indan-2-ylamine and N-(2-benzyloxy-5-bromoacetyl-phenyl)-methanesulfonamide is stirred in acetonitrile at room temperature for 20 hours. The product is isolated by filtration. ES+ MS m/e 479 (MH+)

(b) N-[2-Benzyloxy-5-[2-(2-ethyl-indan-2-ylamino)-1-hydroxy-ethyl]-phenyl]-methanesulfonamide The product of Example 34(a) is suspended in a mixture of ethanol and dichloromethane. Sodium borohydride is added at 0° C. and the mixture stirred at room temperature for 3 hours, then filtered and chromatographed (silica, ethylacetate/ethanol 4:1) to give a white foam. ES+ MS m/e 480 (MH+)

(c) N-[5-[2-(2-Ethyl-indan-2-ylamino)-1-hydroxy-ethyl]-2-hydroxy-phenyl]-methanesulfonamide The product of Example 34(b) (0.29 g) in methanol (20 mL) is stirred under hydrogen in the presence of 10% Pd/C at room temperature for 18 hours. The mixture is filtered through celite and the filtrate is concentrated in vacuo, then chromatographed (silica, ethyl acetate/ethanol 2:1). After trituration with ether/ethyl acetate off-white crystals (100 mg) are obtained.
$^1$H-NMR (d$_4$-CH$_3$OH) ppm: 0.85 (t, 3H), 1.65 (m, 2H), 2.75 (m, 2H), 2.85 (s, 3H), 2.95 (m, 4H), 6.80 (d, 1H), 7.05 (m, 5H), 7.30 (s, 1H).
ES+ MS m/e 491 (MH+)

EXAMPLE 35

(a) Acetic acid (R)-1-(4-benzyloxy-3-methanesulfonylamino-phenyl)-2-[benzyl-(2,5,6-trimethyl-indan-2-yl)-amino]-ethyl ester To a solution of Intermediate 29 in dichloromethane and triethylamine at room temperature is added methanesulfonyl chloride and the mixture stirred for 18 hours. It is then washed with 0.2 N HCl, saturated NaHCO$_3$ solution and brine. The product is purified by chromatography (silica, ethyl acetate/hexane 1:4). ES+ MS m/e 625 (M+)

(b) N-(2-Benzyloxy-5-[(R)-2-[benzyl-(2,5,6-trimethyl-indan-2-yl)-amino]-1-hydroxy-ethyl]-phenyl)-methanesulfonamide The product of Example 35(a) is stirred in methanol/water with K$_2$CO$_3$ for 3 days then solvents removed in vacuo. The product is purified by chromatography (silica, ethyl acetate/hexane 1:2).
$^1$H-NMR (CDCl$_3$) ppm: 1.21 (s, 3H), 2.22 (s, 6H), 2.63-2.82 (m, 4H), 2.84 (s, 3H), 3.20 (br.d, 2H), 3.61 (d, 1H), 3.64 (br.s., 1H), 3.83 (m, 1H), 4.08 (d, 1H), 5.09 (s, 2H), 6.75 (br.s, NH), 6.90-7.05 (m, 4H), 7.25-7.45 (11H).

(c) N-{2-Hydroxy-5-[(R)-1-hydroxy-2-(2,5,6-trimethyl-indan-2-ylamino)-ethyl}-phenyl]-methanesulfonamide is prepared from the product of Example 35(b) by a procedure analogous to that of Example 34(c). ES+ MS m/e 405 (MH+)

What is claimed:

1. A capsule that contains a pharmaceutical composition comprising:
   (A) (R)-5-[2-(5,6-diethyl-indan-2-ylamino)-1-hydroxy-ethyl]-8-hydroxy-1H-quinolin-2-one or a salt or solvate thereof;
   (B) an anticholinergic or antimuscarinic agent; and
   (C) a pharmaceutically acceptable carrier.

2. A capsule according to claim 1, in which (A), (B) and (C) contained therein are in inhalable form.

3. A capsule according to claim 2, in which the pharmaceutical composition contained therein is a dry powder formulation.

4. A capsule according to claim 3 that contains a daily dose of (A) and a daily dose of (B).

5. A capsule according to claim 4, in which the daily dose of (A) is from 1 µg to 5000 µg.

6. A capsule according to claim 1, in which (A) is (R)-5-[2-(5,6-diethyl-indan-2-ylamino)-1-hydroxy-ethyl]-8-hydroxy-1H-quinolin-2-one maleate.

7. A capsule according to claim 5, in which (A) is (R)-5-[2-(5,6-diethyl-indan-2-ylamino)-1-hydroxy-ethyl]-8-hydroxy-1H-quinolin-2-one maleate.

8. A capsule according to claim 1, in which (B) is selected from the group consisting of ipratropium bromide, oxitropium bromide and tiotropium bromide.

9. A capsule according to claim 8, in which (B) is tiotropium bromide.

10. A capsule according to claim 4, in which (B) is selected from the group consisting of ipratropium bromide, oxitropium bromide and tiotropium bromide.

11. A capsule according to claim 10, in which (B) is tiotropium bromide.

12. A capsule according to claim 1, in which (A) is (R)-5-[2-(5,6-diethyl-indan-2-ylamino)-1-hydroxy-ethyl]-8-hydroxy-1H-quinolin-2-one maleate and (B) is selected from the group consisting of ipratropium bromide, oxitropium bromide and tiotropium bromide.

13. A capsule according to claim 1, in which (A) is (R)-5-[2-(5,6-diethyl-indan-2-ylamino)-1-hydroxy-ethyl]-8-hydroxy-1H-quinolin-2-one maleate and (B) is tiotropium bromide.

* * * * *